US009486163B2

(12) United States Patent
Acosta et al.

(10) Patent No.: US 9,486,163 B2
(45) Date of Patent: Nov. 8, 2016

(54) SILICON-VACANCY-DOPED NANODIAMONDS FOR MOLECULAR AND CELLULAR IMAGING

(71) Applicant: Verily Life Sciences LLC, Mountain View, CA (US)

(72) Inventors: Victor Marcel Acosta, San Francisco, CA (US); Vikram Singh Bajaj, Mountain View, CA (US); Andrew Homyk, Redwood City, CA (US); Eric Peeters, San Jose, CA (US); Jason Donald Thompson, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 55 days.

(21) Appl. No.: 14/186,937

(22) Filed: Feb. 21, 2014

(65) Prior Publication Data

US 2015/0238125 A1  Aug. 27, 2015

(51) Int. Cl.
*A61B 5/1459* (2006.01)
*A61B 5/00* (2006.01)
(Continued)

(52) U.S. Cl.
CPC .......... *A61B 5/1459* (2013.01); *A61B 5/0071* (2013.01); *A61B 5/0075* (2013.01); *A61B 5/1455* (2013.01); *A61B 5/1468* (2013.01); *A61B 5/1477* (2013.01); *A61B 5/14532* (2013.01); *A61B 5/14546* (2013.01); *A61B 5/14558* (2013.01); *A61B 5/681* (2013.01);
(Continued)

(58) Field of Classification Search
None
See application file for complete search history.

(56) References Cited

U.S. PATENT DOCUMENTS 4,819,646 A * 4/1989 Cheung et al. ............... 600/323
6,615,063 B1 * 9/2003 Ntziachristos et al. ...... 600/312
(Continued)

FOREIGN PATENT DOCUMENTS

WO  2013/066446  5/2013
WO  2013/188651  12/2013

OTHER PUBLICATIONS

V. Vaijayanthimala, P CHeng, S Yeh, K Liu, C Hsiao, J Chao, H CHang, "The long-term stability and biocompatibility of fluorescent nanodiamond as an in vivo contrast agent", Biomaterials 33, 2012.*
(Continued)

*Primary Examiner* — Tse Chen
*Assistant Examiner* — Joanne Hoffman
(74) *Attorney, Agent, or Firm* — McDonnell Boehnen Hulbert & Berghoff LLP

(57) ABSTRACT

An imaging agent for detecting analytes in a biological environment includes functionalized, silicon vacancy center-containing nanodiamonds. Individual nanodiamonds of the imaging agent include at least one silicon vacancy center. The at least one silicon vacancy center can emit light having a wavelength in a narrow band in response to illumination having any wavelength in a wide range of wavelengths. The nanodiamonds are functionalized to selectively interact with an analyte of interest. The nanodiamonds can additionally include other color centers, and the imaging agent can include a plurality of sets of nanodiamonds having detectably unique ratios of silicon vacancy centers to other color centers. The silicon vacancy centers in the nanodiamonds can have a preferred orientation enabling orientation tracking of individual nanodiamonds or other applications. A method for detecting properties of the analyte of interest by interacting with the imaging agent is also provided.

15 Claims, 15 Drawing Sheets

(51) Int. Cl.
| | | |
|---|---|---|
| A61B 5/145 | (2006.01) | |
| A61B 5/1455 | (2006.01) | |
| A61B 5/1468 | (2006.01) | |
| A61B 5/1477 | (2006.01) | |
| A61K 49/00 | (2006.01) | |
| G01N 21/64 | (2006.01) | |
| B82Y 30/00 | (2011.01) | |
| C09K 11/59 | (2006.01) | |
| C23C 16/27 | (2006.01) | |
| G01R 33/28 | (2006.01) | |
| G01R 33/56 | (2006.01) | |
| G02B 21/00 | (2006.01) | |
| G01N 21/17 | (2006.01) | |
| B82Y 5/00 | (2011.01) | |
| B82Y 15/00 | (2011.01) | |

(52) U.S. Cl.
CPC ............. *A61B 5/7282* (2013.01); *A61B 5/742* (2013.01); *A61B 5/746* (2013.01); *A61B 5/7475* (2013.01); *A61K 49/0013* (2013.01); *A61K 49/0093* (2013.01); *G01N 21/6458* (2013.01); *A61B 5/0022* (2013.01); *A61B 5/4848* (2013.01); *B82Y 5/00* (2013.01); *B82Y 15/00* (2013.01); *B82Y 30/00* (2013.01); *C09K 11/59* (2013.01); *C23C 16/27* (2013.01); *G01N 2021/1746* (2013.01); *G01R 33/281* (2013.01); *G01R 33/5601* (2013.01); *G02B 21/00* (2013.01)

(56) References Cited

U.S. PATENT DOCUMENTS

| | | | |
|---|---|---|---|
| 8,168,413 B2 | 5/2012 | Chang et al. | |
| 8,193,808 B2 | 6/2012 | Fu et al. | |
| 8,617,824 B2 | 12/2013 | Poetter et al. | |
| 2005/0019955 A1 | 1/2005 | Dahl et al. | |
| 2006/0287603 A1* | 12/2006 | Bartnik et al. | 600/504 |
| 2007/0172427 A1* | 7/2007 | Barchi, Jr. | A61K 39/0011 424/9.34 |
| 2010/0181534 A1 | 7/2010 | Shenderova et al. | |
| 2010/0324385 A1 | 12/2010 | Moon et al. | |
| 2011/0062957 A1 | 3/2011 | Fu et al. | |
| 2012/0019242 A1 | 1/2012 | Hollenberg et al. | |
| 2013/0115647 A1 | 5/2013 | Rogers et al. | |
| 2014/0099007 A1* | 4/2014 | Sarkar | G06T 5/003 382/128 |

OTHER PUBLICATIONS

T.D. Merson, S. Castelletto, I. Aharonovich, A. Turbic, T. J. Kilpatrick, A. M. Turnley, "Nanodiamonds with silicon vacancy defects fornon-toxic photostable fluorescent laeling of neural percursor cells", Optics letters, 38:20, 2013.*

C. Fu, H. Lee, K. Chen, T. Lim, H. Wu, P. Lin, P. Wei, P. Tsao, H. Chang, W. Fann, "Characterization and application of single fluorescent nanodiamonds as cellular biomarkers", PNAS, 104(2), 2007.*

E. Neu, M. Agio, C. Becher, "Photophysics of single silicon vacancy centers in diamond: implications for single photon emision", Optical Society of America, 2012.*

S. Singh and S. Satledge, "Strong Narrow-Band Luminescence from Silicon-Vacancy Color Centers in Spatially Localized Sub-10 nm Nanodiamond", Adv Sci Lett, 4(2), 2011.*

C. Hepp, T. Muller, V. Waselowski, J. Becker, B. Pingault, H. Sternschulte, D. Steinmuller-Nethl, A. Gali, J. Maze, M. Atature, B. Becher, "The electronic structure of the silicon vacancy color center in diamond", Physical Review Letters, 2013.*

Catledge, "Silicon vacancy color center photoluminescence enhancement in nanodiamond particles by isolated substitutional nitrogen on {100} surfaces", Journal of Applied Physics 113, pp. 1-6, 2013.*

Smith, "Multicolor quantum dots for molecular diagnostics of cancer", Expert Rev. Mol Diagn., 6(2), pp. 231-244, 2006.*

A. M. Edmonds et al., "Production of oriented nitrogen-vacancy color centers in synthetic diamond", arXiv:1112.5757 [cond-mat. mtrl-sci], Dec. 24, 2011.

Lachlan J. Rogers et al., "Electronic structure of the negatively-charged silicon-vacancy center in diamond", arXiv:1310.3131v1, [cond-mat.mtrl-sci], Oct. 11, 2013.

Chi-Cheng Fu et al., "Characterization and application of single fluorescent nanodiamonds as cellular biomarkers", Proc. Natl. Acad. Sci. U.S.A., vol. 104, No. 3, Jan. 16, 2007.

Christian Hepp et al., "The electronic structure of the silicon vacancy color center in diamond", arXiv:1310.3106v1, [cond-mat. mtrl-sci], Oct. 11, 2013.

International Searching Authority, International Search Report and Written Opinion for PCT/US2015/015046 mailed May 21, 2015, 9 pages.

* cited by examiner

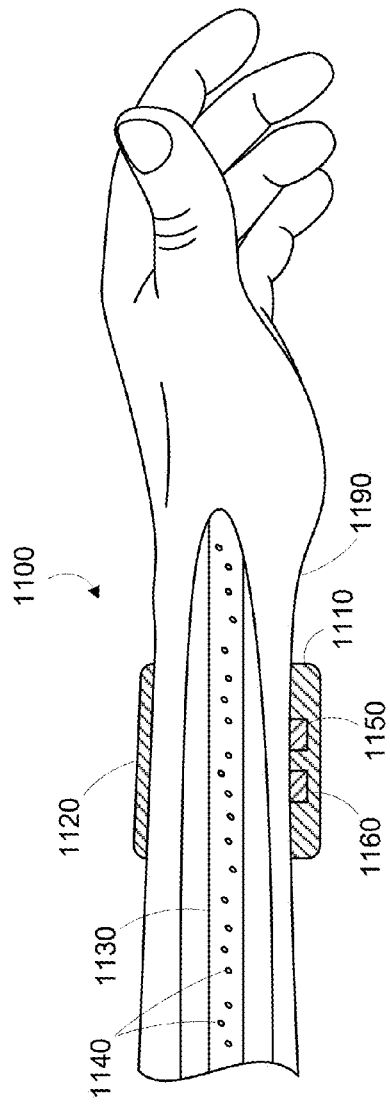
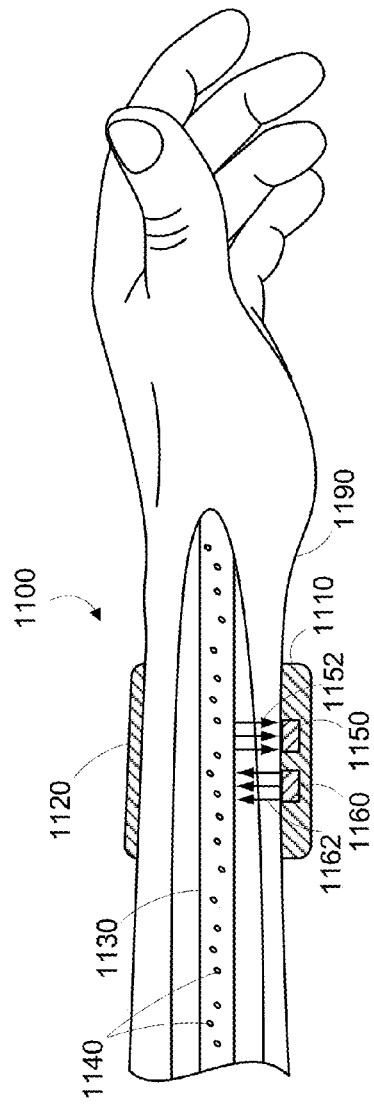

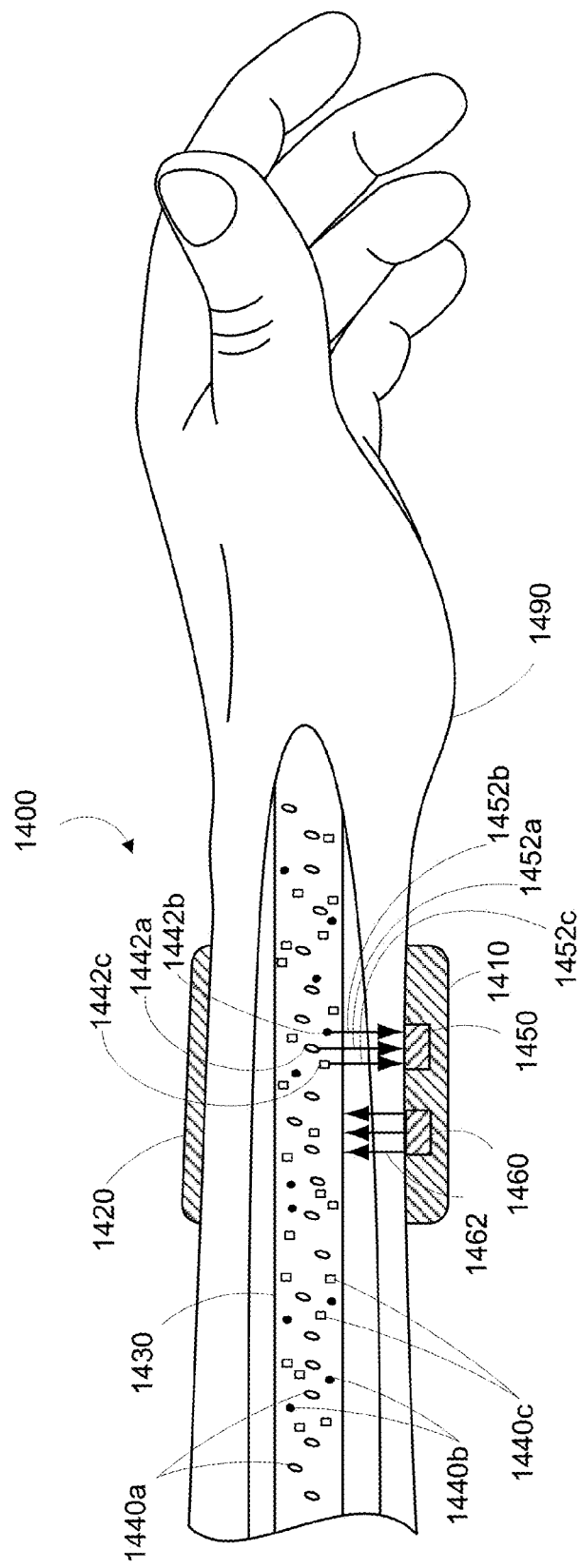

SILICON-VACANCY-DOPED NANODIAMONDS FOR MOLECULAR AND CELLULAR IMAGING

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a biological or other environment. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout an animal's body was of scientific interest. The one or more analytes could be cofactors, substrates, products, or other substances related to a drug under development. The one or more analytes could be present in living or nonliving human or animal tissue, and could be detected and/or measured in an in vivo, ex vivo, in vitro, or some other type of sample. The one or more analytes could include enzymes, reagents, hormones, proteins, cells or other molecules.

Detecting and/or measuring one or more analytes in a biological or other environment can be accomplished through the use of an imaging or contrast agent targeted to the one or more analytes. The contrast agent can facilitate detection and/or measurement of the one or more analytes by having an optical, magnetic, electromagnetic, acoustical, and/or some other property that is detectably different from the surrounding environment. Detection of the targeted contrast agent in the environment could be used as a proxy for detection of the one or more analytes. For example, the contrast agent could absorb light of a first wavelength and emit light of a second wavelength in response to absorbing the light of the first wavelength. The contrast agent could be detected by emitting light of the first wavelength into the environment (e.g., a lumen of vasculature of a person's body) and detecting light of the second wavelength that is emitted from the environment in response to emitting the light of the first wavelength.

SUMMARY

Some embodiments of the present disclosure provide a method including: (i) exposing a biological environment to illumination, wherein the biological environment includes silicon-vacancy nanodiamonds, wherein each of the silicon-vacancy nanodiamonds has at least one silicon vacancy center and is functionalized to selectively interact with an analyte in the biological environment, and wherein the illumination causes the silicon vacancy centers to emit light; and (ii) detecting one or more properties of the light emitted by the silicon vacancy centers in response to the illumination.

Some embodiments of the present disclosure provide an imaging agent including a plurality of functionalized nanodiamonds, wherein the plurality of functionalized nanodiamonds includes a plurality of functionalized silicon-vacancy nanodiamonds, wherein each functionalized silicon-vacancy nanodiamond has at least one silicon vacancy center, wherein each functionalized silicon-vacancy nanodiamond includes a targeting agent configured to selectively bind with a target analyte in a biological environment.

Some embodiments of the present disclosure provide a device including: (i) a light source configured to expose a biological environment to illumination, wherein the biological environment includes silicon-vacancy nanodiamonds, wherein each silicon-vacancy nanodiamond has at least one silicon vacancy center and is functionalized to selectively interact with an analyte in the biological environment, and wherein the silicon vacancy centers are configured to emit light in response to the illumination; and (ii) a light sensor configured to detect one or more properties of the light emitted by the silicon vacancy centers in response to the illumination.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 11A is side partial cross-sectional view of a wrist-mounted device, while on a human wrist.

FIG. 11B is side partial cross-sectional view of a wrist-mounted device, while on a human wrist.

FIG. 14 is side partial cross-sectional view of a wrist-mounted device, while on a human wrist.

DETAILED DESCRIPTION

Figure 1:
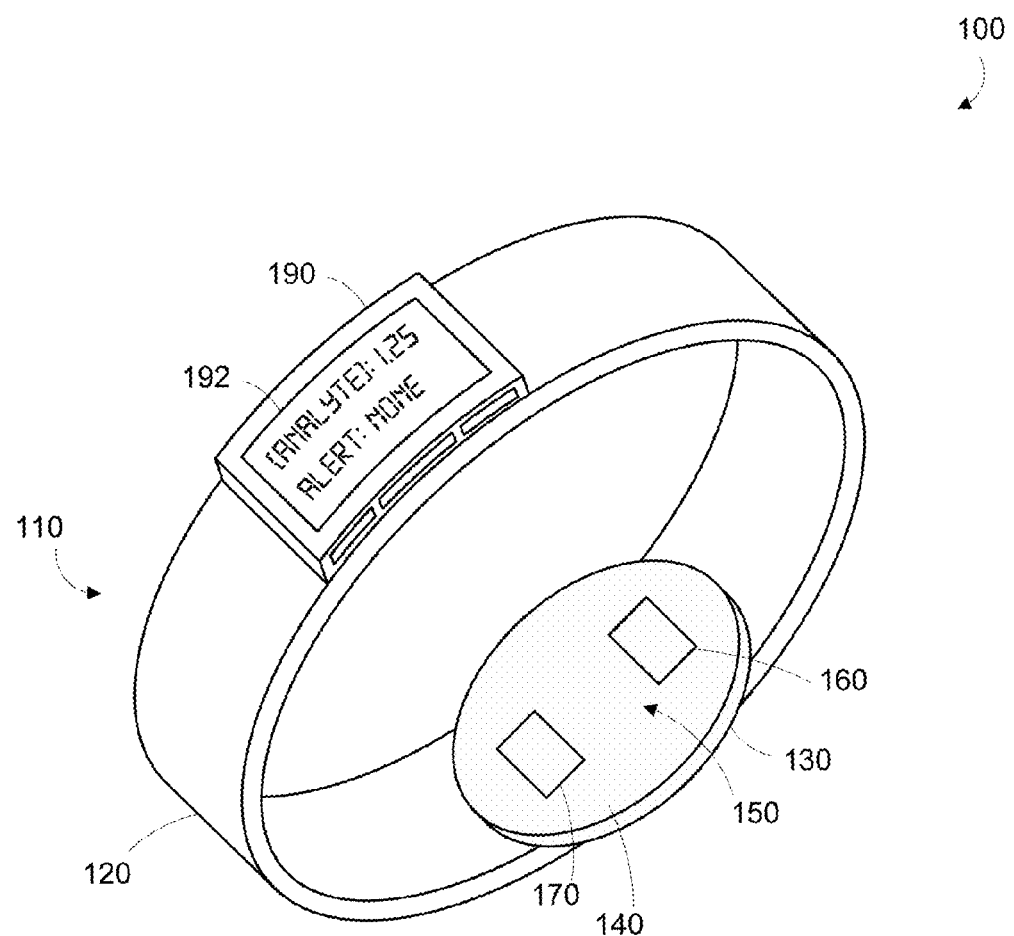
FIG. 1 is a perspective view of an example wearable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vitro applications are possible as well. Accordingly, the environment may also include a test tube or other vessel for holding a fluid.

I. Overview

An imaging agent including functionalized, silicon vacancy center doped nanodiamonds could be used to determine the presence, concentration, and/or other properties of one or more analytes in a biological environment (e.g., an environment within a human body). Individual silicon vacancy centers (sometimes referred to as silicon vacancy color centers, silicon vacancy defects, or silicon color centers) in diamond can be illuminated by light having any wavelength in a wide range of wavelengths (e.g., from about 500 nanometers to about 750 nanometers for single-photon excitation or from about 1000 nanometers to about 1200 nanometers for two-photon excitation) and can emit light having a wavelength of approximately 738 nanometers in response to the illumination. The imaging agent could be functionalized with receptors, proteins, antibodies, DNA sequences, and/or other materials such that the imaging agent selectively interacts with the one or more analytes.

The imaging agent could be introduced into a biological environment. Light could be directed into the environment such silicon vacancy centers in the nanodiamonds of the imaging agent emit light having a wavelength of approximately 738 nanometers. The silicon vacancy centers could include negatively-charged silicon vacancy centers, neutral silicon vacancy centers, positively charged silicon vacancy centers, and multiply charged silicon vacancy center. Silicon vacancy centers having different charge states can have different respective optical properties. One or more properties of the emitted light could be detected and used to determine one or more properties of the imaging agent in the environment (e.g., the location of individual nanodiamonds of the imaging agent). The determined one or more properties of the imaging agent in the biological environment could be used to determine the presence, location, concentration, and/or other properties of the one or more analytes in the biological environment. For example, the biological environment could be a human body and the one or more analytes could be cancer cells. The imaging agent could be functionalized to selectively bind to the cancer cells and/or to elements of the cancer cells. The presence of the cancer cells in the human body could be detected by detecting one or more properties of the imaging agent in the human body.

The imaging agent could include nanodiamonds having nitrogen vacancy centers (sometimes referred to as nitrogen vacancy color centers, nitrogen vacancy defects, or nitrogen color centers). Nitrogen vacancy centers in diamond can emit light in response to illumination, and the optical properties of the nitrogen vacancy centers (e.g., wavelength of emitted light, polarization of emitted light, wavelength of illuminating light) can be different from the optical properties of silicon vacancy centers in diamond. The relative amount of silicon vacancy centers and nitrogen vacancy centers in an individual nanodiamond could be determined using differences in the optical properties of nitrogen vacancy centers and silicon vacancy centers. The nitrogen vacancy centers could be negatively, positively, or multiply charged, or could have no (neutral) charge. Nitrogen vacancy centers having different charge states can have different respective optical properties.

The imaging agent could include multiple populations of functionalized nanodiamonds wherein individual populations of nanodiamonds have detectably unique amounts of nitrogen vacancy centers and silicon vacancy centers. For example, an imaging agent could include a first population of functionalized nanodiamonds that selectively interacts with a first analyte and that has a first ratio of nitrogen vacancy center concentration to silicon vacancy center concentration. The imaging agent could further include a second population of functionalized nanodiamonds that selectively interacts with a second analyte and that has a second ratio of nitrogen vacancy center concentration to silicon vacancy center concentration. The identity of an analyte bound to an individual functionalized nanodiamond could be determined using a determination of whether a detected individual nanodiamond had the first ratio or the second ratio of nitrogen vacancy center concentration to silicon vacancy center concentration. Other sets of populations of nanodiamonds in an imaging agent and other methods for determining the presence, concentration, identity, and/or other properties of an analyte are anticipated.

Silicon vacancy centers (SiV centers) in nanodiamond can absorb and/or emit light in a polarization-dependent manner. That is, an individual SiV center could absorb more light of a first polarization relative to the orientation of the SiV center than light of a second polarization. Similarly, an individual SiV center can be more likely to emit light having a specific polarization relative to the orientation of the SiV center than light of other polarizations. An imaging agent could include functionalized nanodiamonds that individually have a single SiV center or that individually have multiple SiV centers where the multiple SiV centers have a preferred orientation within the individual nanodiamond. The imaging agent could be illuminated by light having a particular polarization and the emitted intensity of the light emitted by the SiV centers of the imaging agent in response to the illumination could be detected. Additionally or alternatively, the polarization of the light emitted by the imaging agent in response to illumination could be detected. This method could be used to detect the imaging agent in high-noise and/or low-signal-to-noise-ratio environments. Additionally or alternatively, this method could be used to detect the orientation of individual nanodiamonds of the imaging agent.

The nanodiamonds of the imaging agent can be functionalized by covalently or otherwise attaching or associating a bioreceptor that specifically binds or otherwise interacts with a particular analyte. The bioreceptor can be an antibody, peptide, nucleic acid, phage, bacteria, virus, aptamer or any other molecule with a defined affinity for a target analyte. Other compounds or molecules, such as fluorophores or autofluorescent or luminescent markers or nonoptical contrast agents (e.g. acoustic impedance contrast, RF contrast and the like), which may assist in interrogating the nanodiamonds or particles of an imaging agent including the nanodiamonds in a biological environment, may also be attached to the nanodiamonds.

The imaging agent could include nanoparticles that include other elements in addition to one or more functionalized nanodiamonds as described herein. Those of skill in the art will understand a "particle" in its broadest sense and that it may take the form of any fabricated material, a molecule, tryptophan, a conductive or nonconductive nanorod, a quantum dot, a virus, a phage, a complex of nanodiamonds, etc. Further, a particle may be of any shape, for example, spheres, rods, non-symmetrical shapes, etc.

A system may include one or more data collection systems for interrogating, in a non-invasive manner, functionalized nanodiamonds present in a biological environment, such as a lumen of subsurface vasculature in a particular local area of a human. In one example, the system includes a light sensor configured to detect a response signal transmitted from functionalized nanodiamonds in a portion of subsurface vasculature. In some examples, the system may also include an interrogating light source for transmitting illumination that can penetrate into a portion of subsurface vasculature, or another body system, and a light sensor for detecting an emitted light that is emitted by SiV centers in functionalized nanodiamonds in the portion of subsurface vasculature, or other body system, in response to the illumination.

The above described system may be implemented as a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The light sensor, light source, and, in some examples, a processor, may be provided on the wearable device. In other embodiments, the above described system may be implemented as a stationary measurement device to which a user must be brought into contact or proximity with or as a device that may be temporarily placed or held against a body surface during one or more measurement periods.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Example Devices

A wearable device 100 can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 110, such as a belt, wristband, ankle band, etc. can be provided to mount the device at, on or in proximity to the body surface. The mount 110 may prevent the wearable device from moving relative to the body to reduce measurement error and noise. In one example, shown in FIG. 1, the mount 110, may take the form of a strap or band 120 that can be worn around a part of the body. Further, the mount 110 may be an adhesive substrate for adhering the wearable device 100 to the body of a wearer.

A measurement platform 130 is disposed on the mount 110 such that it can be positioned on the body where subsurface vasculature is easily observable. An inner face 140 of the measurement platform is intended to be mounted facing to the body surface. The measurement platform 130 may house a data collection system 150, which may include at least one detector 160 for detecting at least one physiological parameter, which could include any parameters that may relate to the health of the person wearing the wearable device. For example, the detector 160 could be configured to measure blood pressure, pulse rate, respiration rate, skin temperature, etc. In a non-exhaustive list, detector 160 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 150 may be miniaturized so that the wearable device may be worn on the body without significantly interfering with the wearer's usual activities.

At least one of the detectors 160 is a light sensor configured to detect one or more properties of light emitted by silicon vacancy defects in functionalized silicon vacancy nanodiamonds in blood circulating in subsurface vasculature proximate to the wearable device. The light sensor could include one or more filters to block light of wavelengths other than the line of zero-phonon emission for silicon vacancy centers in nanodiamonds (about 738 nanometers). For example, the light sensor could include a filter that is configured to substantially block light emitted by a light source 170 of the data collection system 150.

The light sensor could be configured to sense the polarization of light and/or to only detect light of a specified polarization. For example, the light sensor could include a linear polarization filter such that the light sensor only detected light having a polarization aligned with the orientation of the linear polarization filter. In some examples, the detectors 160 could include a first light sensor configured to detect light of a first polarization and a second light sensor configured to detect light of a second polarization, where the second polarization is perpendicular to the first polarization. The first and second detectors could be used to determine an orientation of silicon vacancy defects in nanodiamonds by detecting the polarization of light emitted by the silicon vacancy centers.

The detectors 160 could include light sensors configured to detect light not emitted by silicon vacancy centers in nanodiamonds. The light sensors could be configured to detect one or more properties of light emitted by a fluorophore, a color center in a nanodiamond, a Raman dye, a chemiluminescent material, a bioluminescent material, or some other light emitting substance. In some examples, the light sensors could be configured to detect one or more properties of light emitted by nitrogen vacancy centers in nanodiamonds. For example, the light sensors could be configured to detect light having a wavelength between about 550 nanometers and about 800 nanometers, or more preferentially between 650 nanometers and 720 nanometers, to detect one or more properties of light emitted by negatively-charged nitrogen vacancy centers. For example, the light sensors could be configured to detect light having a wavelength of about 700 nanometers, the peak of the emission spectrum for negatively-charged nitrogen vacancy centers in diamond. For example, the light sensors could be configured to detect light having a wavelength of about 576 nanometers and/or about 638 nanometers, corresponding to the first and second zero-phonon lines, respectively, of negatively-charged nitrogen vacancy centers in diamond. Other configurations, types of charged silicon and nitrogen vacancy centers in diamond, and uses of the detectors 160 are anticipated.

In some examples, the data collection system 150 further includes a light source 170 for transmitting illumination that can penetrate the wearer's skin into the portion of subsurface vasculature, for example, into a lumen of the subsurface vasculature. The transmitted illumination can be any kind of illumination that is benign to the wearer and that results at least in emission of light by silicon vacancy defects in functionalized silicon vacancy nanodiamonds proximate to the light source 170. In some examples, the transmitted illumination could have a wavelength between approximately 500 nanometers and approximately 710 nanometers. More particularly, the transmitted illumination could have a wavelength of approximately 532 nanometers or approximately 708 nanometers. In some examples, the transmitted illumination could have a wavelength between approximately 1050 nanometers and approximately 1200 nanometers and could be absorbed by the silicon vacancy centers or by some other light absorbing substance through two-photon absorption. The wavelength of the transmitted illumination could be specified to penetrate biological tissues of a wearer; for example, the transmitted illumination could have a wavelength within one or both of the near-infrared (NIR) transparency windows of biological tissue.

The light source 170 could be configured to produce additional illumination that results in emission of light by other chemicals, imaging agents, biological elements, or other analytes proximate to the light source 170. In some examples, the light source 170 could be configured to produce illumination that results in emission of light by nitrogen vacancy defects in functionalized silicon vacancy nanodiamonds or in other nanodiamonds proximate to the light source 170. For example, the light source 170 could produce illumination having a wavelength of about 532 nanometers in order to cause emission of light by nitrogen vacancy centers in diamond. Additionally or alternatively, the light source 170 could be configured to produce illumination that is able to cause emission of light by silicon vacancy centers in diamond and by nitrogen vacancy centers in diamond. In some examples, the light source 170 could be configured to emit light having a specific polarization relative to the wearable device 100, a wearer of the wearable device, and/or a light sensor included in the detectors 160. For example, the light source 170 could be configured to emit light of a first linear polarization at a first point in time and to emit light of a second linear polarization, where the second linear polarization is perpendicular to the first polarization, at a second point in time. One or more properties of lights emitted by silicon vacancy centers in nanodiamonds in response to illumination by the light source 170 at the first and second points in time could be detected using the detectors 160. One or more properties of the nanodiamonds and/or analytes bound to the nanodiamonds could be determined based on the detected one or more properties of the emitted lights. Other configurations and uses of the light source 170 are anticipated.

The wearable device 100 may also include a user interface 190 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication of the measured physiological parameters, for instance, the concentrations of certain blood analytes being measured.

Figure 2A:
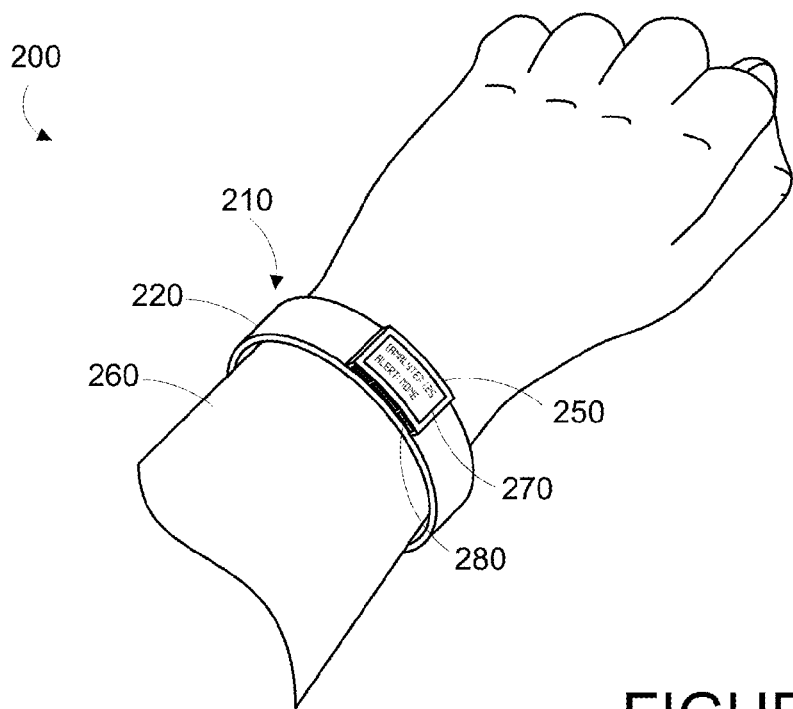
FIG. 2A is a perspective top view of an example wrist-mounted device, when mounted on a wearer's wrist.
Figure 2B:
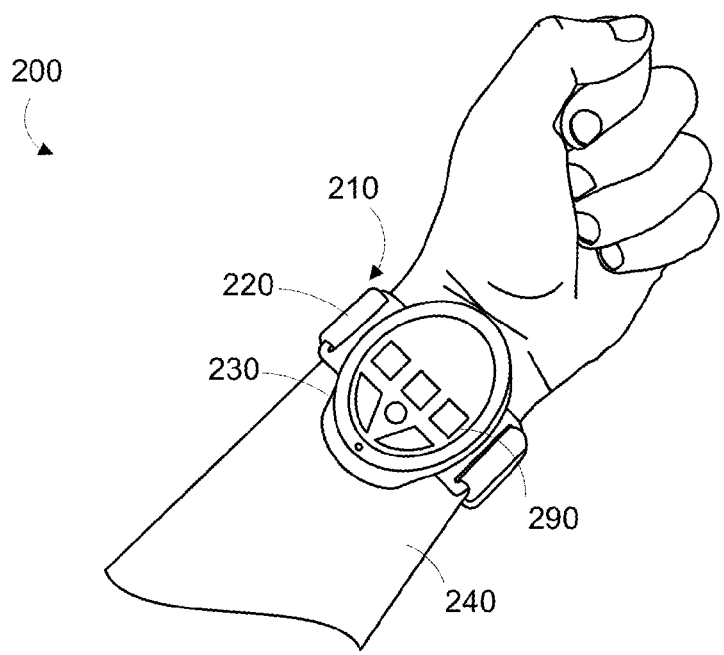
FIG. 2B is a perspective bottom view of an example wrist-mounted device shown in FIG. 2A, when mounted on a wearer's wrist.

In one example, the wearable device is provided as a wrist-mounted device, as shown in FIGS. 2A, 2B, 3A-3C, 4A, 4B, and 5. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a measurement platform 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts from the measurement platform. Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the measurement platform 230 may be located on the anterior side 240 of the wearer's wrist where the subsurface vasculature may be readily observable. However, other configurations are contemplated.

The display 270 may be configured to display a visual indication of the alert or recommendation and/or an indication of the measured physiological parameters, for instance, the presence or concentrations of certain blood analytes being measured. Further, the user interface 250 may include one or more buttons 280 for accepting inputs from the wearer. For example, the buttons 280 may be configured to change the text or other information visible on the display 270. As shown in FIG. 2B, measurement platform 230 may also include one or more buttons 290 for accepting inputs from the wearer. The buttons 290 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 3A:
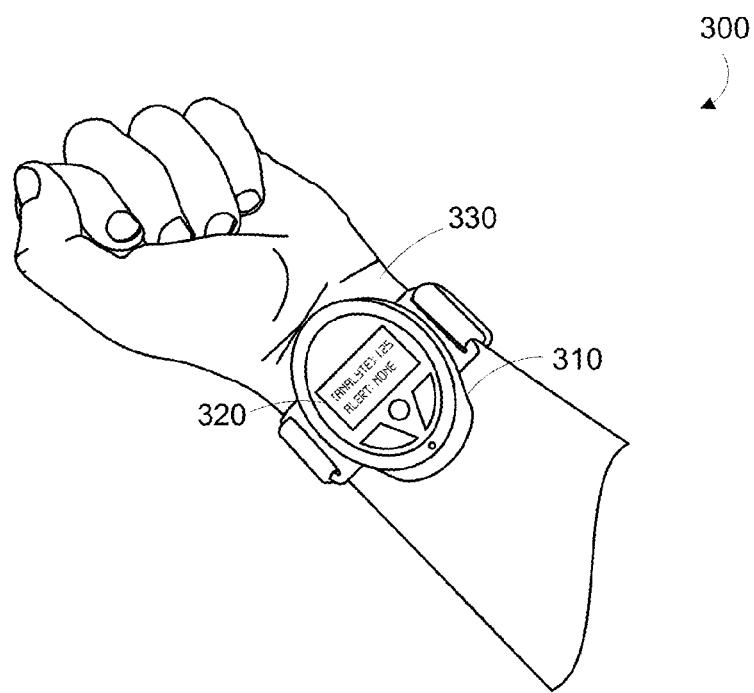
FIG. 3A is a perspective bottom view of an example wrist-mounted device, when mounted on a wearer's wrist.
Figure 3B:
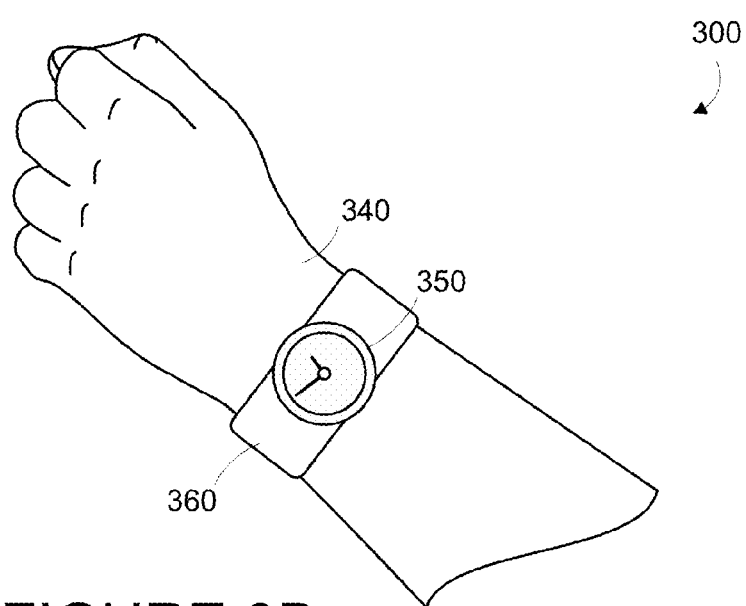
FIG. 3B is a perspective top view of an example wrist-mounted device shown in FIG. 3A, when mounted on a wearer's wrist.
Figure 3C:
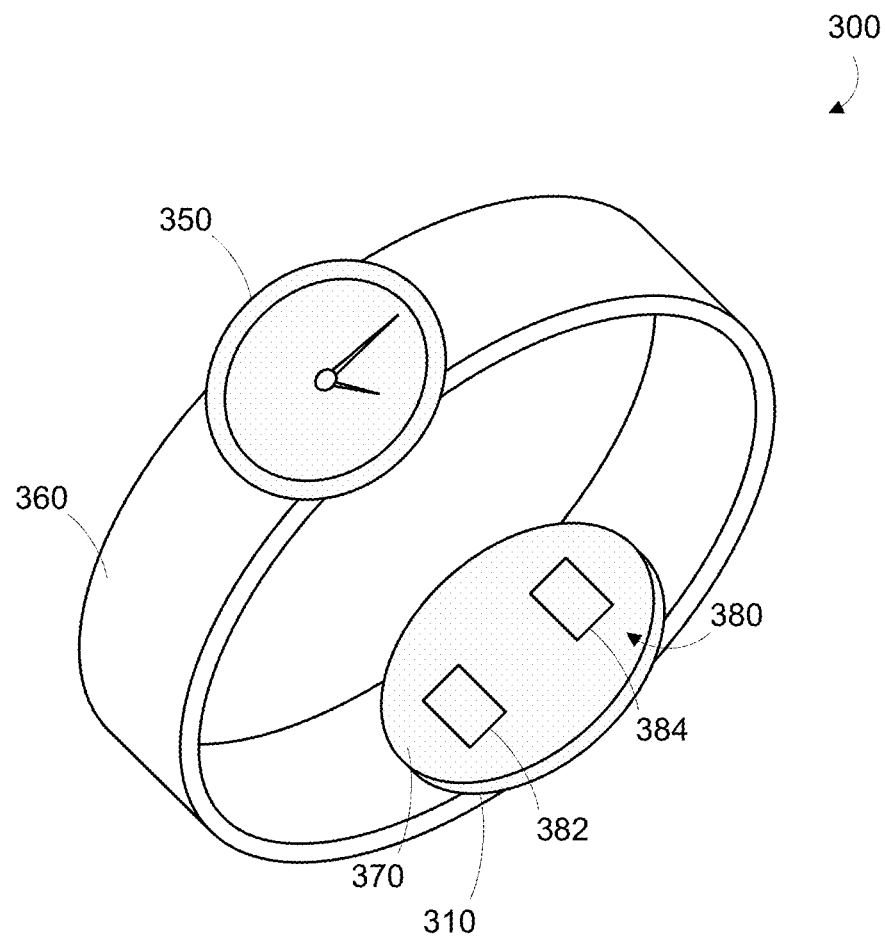
FIG. 3C is a perspective view of an example wrist-mounted device shown in FIGS. 3A and 3B.

In another example wrist-mounted device 300, shown in FIGS. 3A-3C, the measurement platform 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the measurement platform 310 is intended to be worn proximate to the wearer's body. A data collection system 380 housed on the measurement platform 310 may include a detector 382 and a light source 384.

Figure 4A:
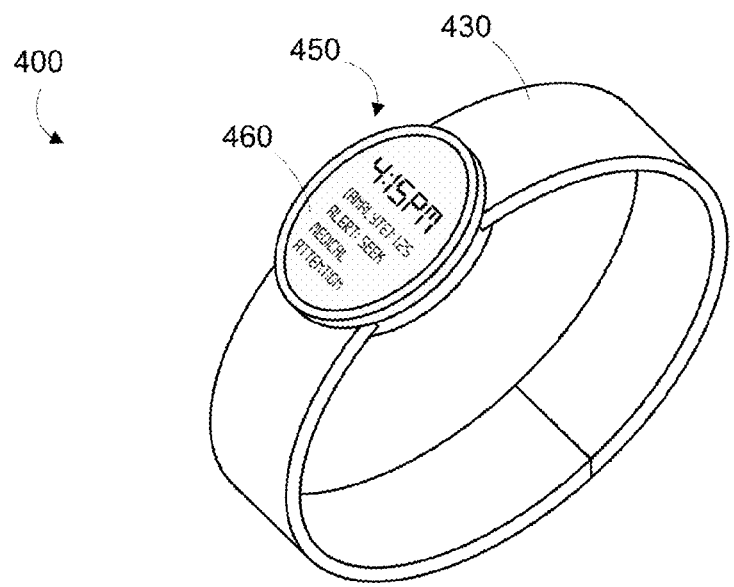
FIG. 4A is a perspective view of an example wrist-mounted device.
Figure 4B:
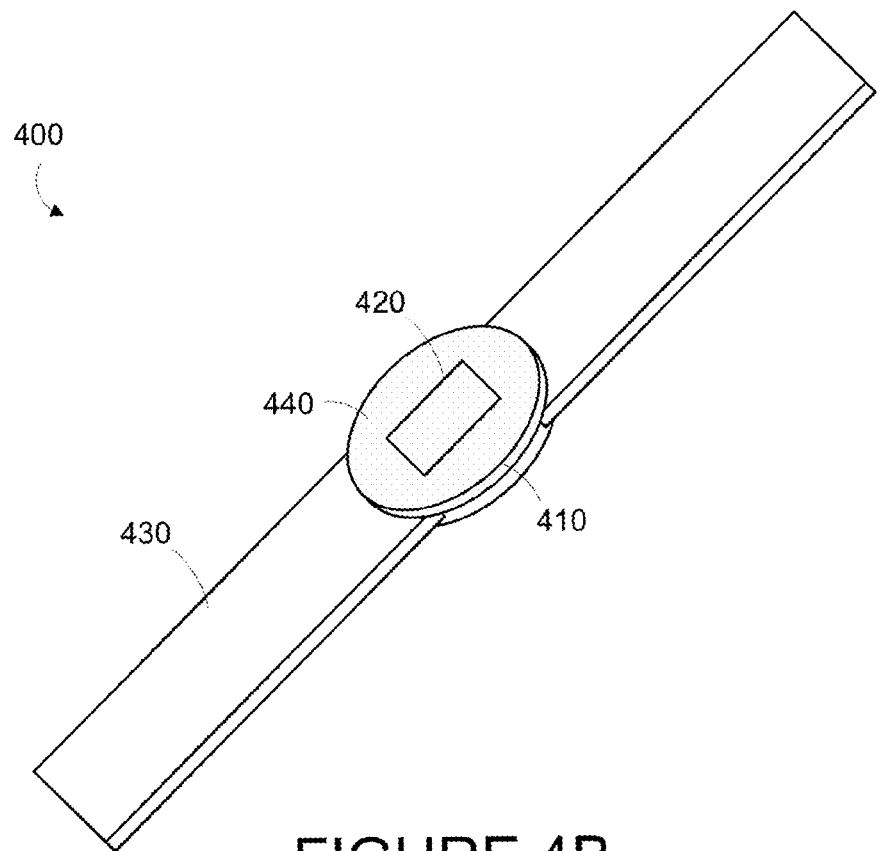
FIG. 4B is a perspective bottom view of an example wrist-mounted device shown in FIG. 4A.

In a further example shown in FIGS. 4A and 4B, a wrist mounted device 400 includes a measurement platform 410, which includes a data collection system 420, disposed on a strap 430. Inner face 440 of measurement platform may be positioned proximate to a body surface so that data collection system 420 may interrogate the subsurface vasculature of the wearer's wrist. A user interface 450 with a display 460 may be positioned facing outward from the measurement platform 410. As described above in connection with other embodiments, user interface 450 may be configured to display data collected from the data collection system 420, including the presence and/or concentration of one or more measured analytes, and one or more alerts generated by a remote server or other remote computing device, or a processor located on the measurement platform. The user interface 420 may also be configured to display the time of day, date, or other information that may be relevant to the wearer.

Figure 5:
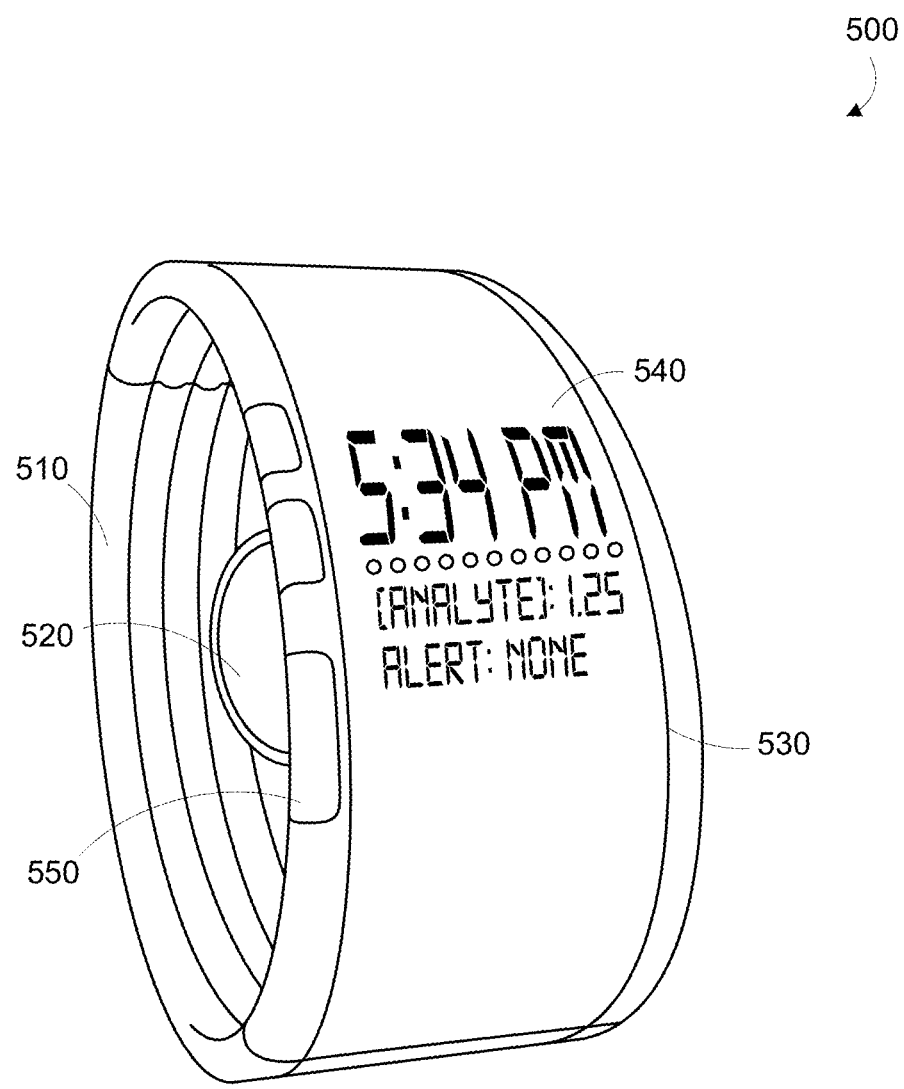
FIG. 5 is a perspective view of an example wrist-mounted device.

As shown in FIG. 5, in a further embodiment, wrist-mounted device 500 may be provided on a cuff 510. Similar to the previously discussed embodiments, device 500 includes a measurement platform 520 and a user interface 530, which may include a display 540 and one or more buttons 550. The display 540 may further be a touch-screen display configured to accept one or more input by the wearer.

Figure 6:
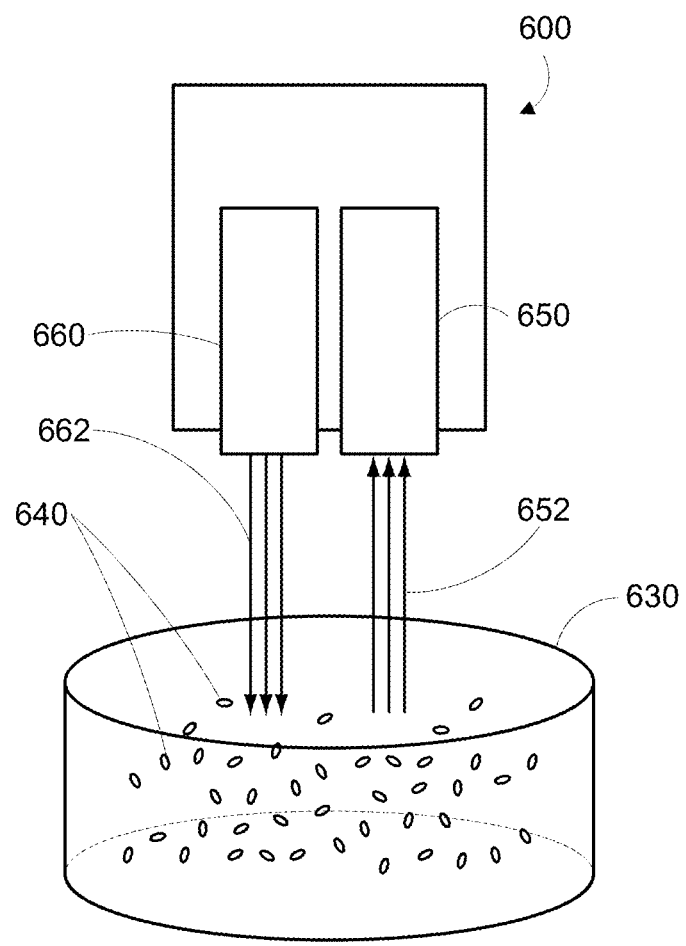
FIG. 6 is a perspective view of an example device.

A device 600 as illustrated in FIG. 6 can determine one or more properties of an analyte in a biological environment 630 by detecting one or more properties of SiV center-containing functionalized nanodiamonds 640 in the environment. The biological environment can be any biological environment containing analytes of interest such that functionalized nanodiamonds 640 in the environment can selectively interact with the analyte of interest and such that SiV centers in the functionalized nanodiamonds can be excited by illumination 662 from the device 600 and at least one property of emitted light 652 emitted by the functionalized nanodiamonds 630 can be detected by the device 600.

The biological environment 630 could be an in vivo biological environment (e.g., a tissue of a living human, animal, plant, etc.) or an in vitro environment. The biological environment 630 could be a biological sample in a sample container, cuvette, pipette, microscope slide, or other vessel. The biological environment 630 could be part of a biological or chemical process. For example, the biological environment could be a fluid in a water treatment process, a fluid in a food or drug preparation process, a lake, stream, or river in a natural environment, a, or some other environment that contained biological material. The biological environment 630 could be a liquid, a gel, a solid, or some other phase of matter or combination of phases (e.g., an emulsion). The biological environment 630 could include biological samples that had been freeze-dried, desiccated, frozen, vaporized, alkalated, or otherwise prepared, including adding the functionalized nanodiamonds 640 to the environment.

The device 600 includes a light sensor 650 configured to detect one or more properties of emitted light 652 emitted by silicon vacancy centers in functionalized silicon vacancy nanodiamonds 630 the biological environment 630 proximate to the device 600. The light sensor 650 could include one or more filters to block light of wavelengths other than the line of zero-phonon emission for silicon vacancy centers in nanodiamonds (about 738 nanometers). For example, the light sensor could include a filter that is configured to substantially block light emitted by a light source 170 of the data collection system 150.

The light sensor 650 could be configured to sense the polarization of light and/or to only detect light of a specified polarization. For example, the light sensor 650 could include a linear polarization filter such that the light sensor only detected light having a polarization aligned with the orientation of the linear polarization filter. The light sensor 650 could additionally or alternatively be configured to only sense light emitted from certain regions of the biological environment 630. For example, the light sensor 650 could include a shaped aperture, optics, diffraction gratings, a mirror mounted on a galvanometer, an actuated mirror, adaptive optics, and/or some other optical components such that the light sensor 630 only detected light from a certain depth or other specified region of the biological environment 630.

The device 600 further includes a light source 660 for transmitting illumination 662 that can penetrate the biological environment 630 and illuminate the functionalized nanodiamonds 640. The transmitted illumination can be any kind of illumination that results at least in emission of light by silicon vacancy defects in the functionalized silicon vacancy nanodiamonds 640 proximate to the device 600. In some examples, the transmitted illumination 662 could have a wavelength between approximately 500 nanometers and approximately 710 nanometers. More particularly, the transmitted illumination 662 could have a wavelength of approximately 532 nanometers or approximately 708 nanometers. In some examples, the transmitted illumination 662 could have a wavelength between approximately 1050 nanometers and approximately 1200 nanometers and could be absorbed by the silicon vacancy centers or by some other light absorbing substance through two-photon absorption. The wavelength of the transmitted illumination 662 could be specified to penetrate a biological tissue in the biological environment; for example, the transmitted illumination 662 could have a wavelength within one or both of the near-infrared (NIR) transparency windows of biological tissue. Exposure to the transmitted illumination 662 could result in damage and/or irreversible damage to elements of the biological environment 662 in examples where the biological environment 630 is not part of a living human or animal or the biological environment 630 does not include samples that cannot be damaged, according to an application.

The light source 650 could be configured to transmit illumination having a specified polarization and/or transmit illumination having different polarizations over time. For example, the light source 660 could include a linear polarization filter such that the light source 660 only transmitted illumination having a polarization aligned with the orientation of the linear polarization filter. The light source 660 could additionally or alternatively be configured to only transmit illumination to illuminate certain regions of the biological environment 630. For example, the light source 660 could include a shaped aperture, optics, diffraction gratings, a mirror mounted on a galvanometer, an actuated mirror, adaptive optics, and/or some other optical components such that the light source 640 illuminated functionalized nanoparticles 640 at a certain depth or other within a specified region of the biological environment 630.

The light sensor 650 and light source 660 could be configured as illustrated in FIG. 6 (i.e., separate, parallel, non-coaxial) or could be configured in another way, according to an application. In some examples, the light sensor 650 and light source 660 could be coupled to a set of optical elements to enable some function. For example, the light source 660 and light sensor 650 could each include an aperture and could be optically coupled to a beam splitter and other optics to enable the device 600 to be operated as a confocal microscope. In another example, the light source 660 could include two light sources configured to produce beams of illumination, where the directions of the beams are controllable using some apparatus, for example a set of galvanometer-driven mirrors. The galvanometers could be operated such that functionalized nanodiamonds 640 in specified regions (where the beams from the light sources overlap) could be illuminated such that silicon vacancy centers, or other color centers, in the functionalized nanodiamonds 640 in the specified regions emitted light. Other configurations and applications are anticipated.

The device 600 could be configured to enable other imaging modalities and/or to operate in concert with other devices configured to enable other imaging modalities. In some examples, the device 600 could include elements to enable magnetic resonance imaging. In some examples, a magnetic field generator could be used to alter properties of color centers in the functionalized nanodiamonds 640 in the biological environment 640 to enable other forms of imaging using the functionalized nanodiamonds 640 and/or to enable the imaging of functionalized nanodiamonds 640 in specific regions of the biological environment 630. Additionally or alternatively, the multiple imaging modalities could be used in a complementary fashion to enable some function. For example, the device 600 could be used to image an analyte (e.g., a cancerous growth) in the biological environment (e.g., a tissue of a human) at the same time magnetic resonance imaging was used to image some other properties of the biological environment (e.g., soft tissue boundaries) in order to perform some manipulation of the biological environment 630 (e.g., a surgical resection of the cancerous growth while minimizing damage to soft tissues surrounding the cancerous growth).

Figure 7:
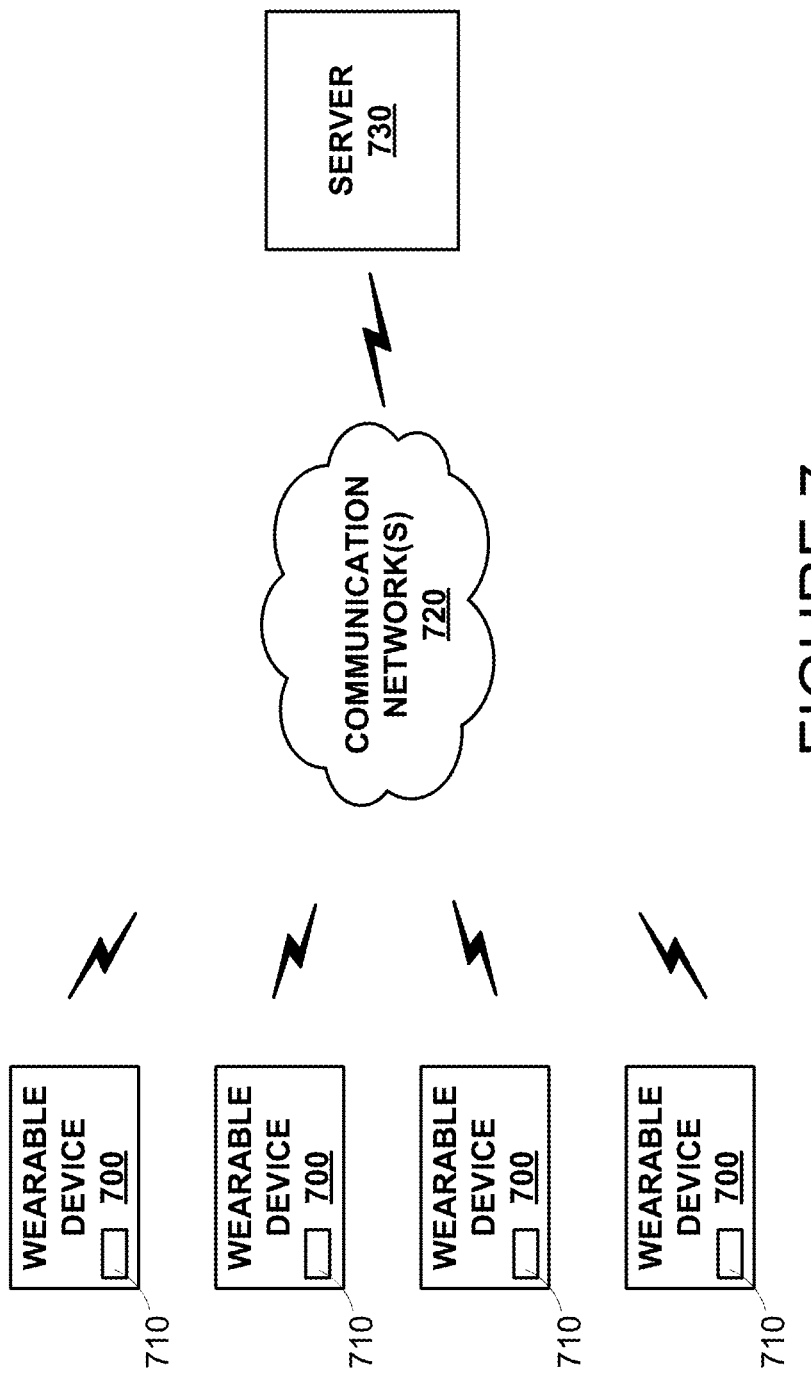
FIG. 7 is a block diagram of an example system that includes a plurality of wearable devices in communication with a server.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Electronics Platform for a Device

Figure 8:
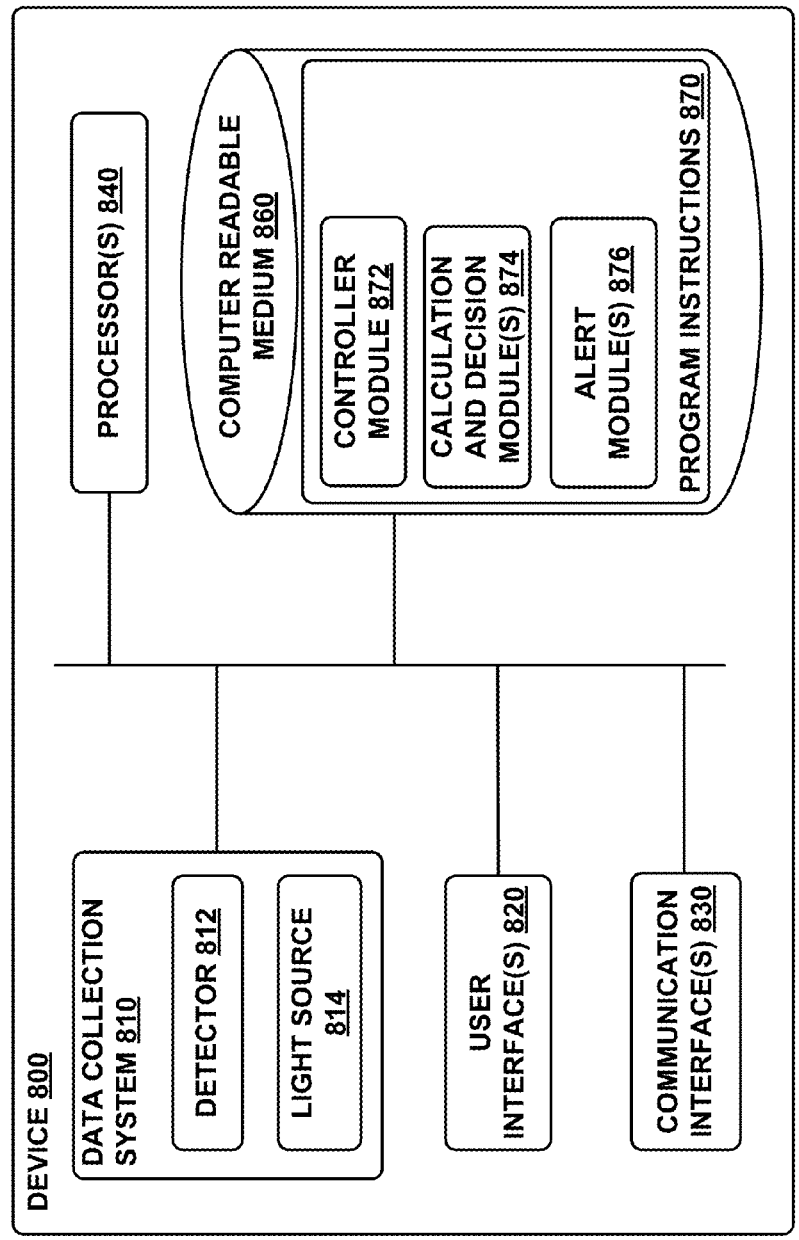
FIG. 8 is a functional block diagram of an example device.

FIG. 8 is a simplified block diagram illustrating the components of a device 800, according to an example embodiment. Device 800 may take the form of or be similar to one of the wrist-mounted devices 200, 300, 400, 500, shown in FIGS. 2A-B, 3A-3C, 4A-4C, and 5, or the device 600 shown in FIG. 6. However, device 800 may also take other forms, such as an ankle, waist, or chest-mounted device. Device 800 could also take the form of a device that is not configured to be mounted to a body. For example, device 800 could take the form of a handheld device configured to be maintained in proximity to a biological environment of interest (e.g., a body part, a biological sample container, a volume of a water treatment system) by a user or operator of the device 800 or by a frame or other supporting structure. Device 800 could also take the form of a device configured to illuminate and to detect emitted light from an in vitro biological environment or some other environment, for example, a fluid volume within a water treatment process. Device 800 could be configured as or part of a microscope, fluorescence microscope, confocal microscope, two-photon microscope, multi-photon microscope, total internal reflection fluorescence microscope, or some other laboratory equipment. Device 800 also could take other forms.

In particular, FIG. 8 shows an example of a wearable device 800 having a data collection system 810, a user interface 820, communication interface 830 for transmitting data to a remote system, and processor(s) 840. The components of the wearable device 800 may be disposed on a mount or on some other structure for mounting the device to an external body surface where a portion of subsurface vasculature is readily observable.

Processor 840 may be a general-purpose processor or a special purpose processor (e.g., digital signal processors, application specific integrated circuits, etc.). The one or more processors 840 can be configured to execute computer-readable program instructions 870 that are stored in the computer readable medium 860 and that are executable to provide the functionality of a device 800 described herein.

The computer readable medium 860 may include or take the form of one or more non-transitory, computer-readable storage media that can be read or accessed by at least one processor 840. The one or more computer-readable storage media can include volatile and/or non-volatile storage components, such as optical, magnetic, organic or other memory or disc storage, which can be integrated in whole or in part with at least one of the one or more processors 840. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

Data collection system 810 includes detectors 812 and a light source 814. As described above, detectors 812 may include any detector capable of detecting at least one biological parameter, which could include any parameters that may relate to the health of a person wearing or otherwise being analyzed by the device. For example, the detectors 812 could be configured to measure blood pressure, pulse rate, skin temperature, etc. In some examples, detectors 812 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

At least one of the detectors 812 is a light sensor configured to detect one or more properties of light emitted by silicon vacancy defects in functionalized silicon vacancy nanodiamonds proximate to the device. The light sensor could include one or more filters to block light of wavelengths other than the line of zero-phonon emission for silicon vacancy centers in nanodiamonds (about 738 nanometers). In some examples, the light sensor could include a filter that substantially blocked light having wavelengths other than wavelengths approximately equal to 738 nanometers. In some examples, the light sensor could include a filter that is configured to substantially block light emitted by the light source 814.

The light sensor could be configured to sense the polarization of light and/or to only detect light of a specified polarization. For example, the light sensor could include a linear polarization filter such that the light sensor only detected light having a polarization aligned with the orientation of the linear polarization filter. In some examples, the detectors 812 could include a first light sensor configured to detect light of a first polarization and a second light sensor configured to detect light of a second polarization, where the second polarization is perpendicular to the first polarization. The first and second detectors could be used to determine an orientation of silicon vacancy centers in nanodiamonds by detecting the polarization of light emitted by the silicon vacancy centers.

The detectors 812 could include light sensors configured to detect light not emitted by silicon vacancy centers in nanodiamonds. The light sensors could be configured to detect one or more properties of light emitted by a fluorophore, a color center in a nanodiamond, a Raman dye, a chemiluminescent material, a bioluminescent material, or some other light emitting substance. For example, the light sensors could be configured to detect one or more properties of light emitted by nitrogen vacancy centers in nanodiamonds. Other configurations and uses of the detectors 812 are anticipated.

In some examples, the data collection system 810 further includes a light source 814 for transmitting illumination that can penetrate a biological environment containing functionalized, silicon vacancy center-containing nanodiamonds, for example, a lumen of the subsurface vasculature of a wearer of the device 800. The transmitted illumination can be any kind of illumination that results at least in emission of light by silicon vacancy centers in functionalized silicon vacancy nanodiamonds in the lumen of the subsurface vasculature of the wearer. In some examples, the transmitted illumination could have a wavelength between approximately 500 nanometers and approximately 710 nanometers. More particularly, the transmitted illumination could have a wavelength of approximately 532 nanometers or approximately 708 nanometers. In some examples, the transmitted illumination could have a wavelength between approximately 1050 nanometers and approximately 1200 nanometers and could be absorbed by the silicon vacancy centers or by some other light absorbing substance through two-photon absorption. The wavelength of the transmitted illumination could be specified to penetrate biological tissues of a wearer; for example, the transmitted illumination could have a wavelength within one or both of the near-infrared (NIR) transparency windows of biological tissue.

The light source 814 could be configured to produce additional illumination that results in emission of light by other chemicals, imaging agents, biological elements, or other analytes on or within a wearer. For example, the light source 814 could be configured to produce illumination that results in emission of light by nitrogen vacancy defects in functionalized silicon vacancy nanodiamonds or in other nanodiamonds in the lumen of the subsurface vasculature of the wearer. In some examples, the light source 814 could be configured to emit light having a specific polarization relative to the device 800, a biological environment or organ of the wearer, and/or a light sensor included in the detectors 812. For example, the light source 814 could be configured to emit light of a first linear polarization at a first point in time and to emit light of a second linear polarization, perpendicular to the first polarization, at a second point in time. One or more properties of lights emitted by silicon vacancy centers in nanodiamonds in response to illumination by the light source 814 at the first and second points in time could be detected using the detectors 812. One or more properties of the nanodiamonds and/or analytes bound to the nanodiamonds could be determined based on the detected one or more properties of the emitted lights. Other configurations and uses of the light source 814 are anticipated.

The program instructions 870 stored on the computer readable medium 860 may include instructions to perform or facilitate some or all of the device functionality described herein. For instance, in the illustrated embodiment, program instructions 870 include a controller module 872, calculation and decision module 874 and an alert module 876.

The controller module 872 can include instructions for operating the data collection system 810, for example, the detectors 812 and light source 814. For example, the controller 872 may operate light source 814 and/or detectors 812 during each of a set of pre-set measurement periods. In particular, the controller module 872 can include instructions for operating the light source 814 to emit illumination into a tissue of a wearer of the wearable device 800 and controlling the detectors 812 to detect one or more properties of light emitted by silicon vacancy centers in nanodiamonds in the tissue of the wearer.

The controller module 872 can also include instructions for operating a user interface 820. For example, controller module 872 may include instructions for displaying data collected by the data collection system 810 and analyzed by the calculation and decision module 874, or for displaying one or more alerts generated by the alert module 875. Further, controller module 872 may include instructions to execute certain functions based on inputs accepted by the user interface 820, such as inputs accepted by one or more buttons disposed on the user interface.

Communication platform 830 may also be operated by instructions within the controller module 872, such as instructions for sending and/or receiving information via a wireless antenna, which may be disposed on or in the device 800. The communication interface 830 can optionally include one or more oscillators, mixers, frequency injectors, etc. to modulate and/or demodulate information on a carrier frequency to be transmitted and/or received by the antenna. In some examples, the device 800 is configured to indicate an output from the processor by modulating an impedance of the antenna in a manner that is perceivable by a remote server or other remote computing device.

Calculation and decision module 872 may include instructions for receiving data from the data collection system 810, analyzing the data to determine if a target analyte is present or absent, quantify the measured physiological parameter(s), such as concentration of a target analyte, analyzing the data to determine if a medical condition is indicated, or other analytical processes relating to the biological environment proximate to the device 800. In particular, the calculation and decision module 872 may include instructions for determining, for each preset measurement time, the presence, concentration, and/or other properties of a clinically-relevant analyte based on the one or more properties of light emitted by silicon vacancy centers in nanodiamonds in the lumen of the subsurface vasculature of the wearer; and determining whether a medical condition is indicated based on at least the corresponding presence, concentration, or other property of the clinically-relevant analyte. These instructions could be executed at each of a set of preset measurement times.

The program instructions of the calculation and decision module 872 may, in some examples, be stored in a computer-readable medium and executed by a processor located external to the device 800. For example, the device 800 could be configured to collect certain data regarding physiological parameters from the wearer and then transmit the data to a remote server, which may include a mobile device, a personal computer, the cloud, or any other remote system, for further processing.

The computer readable medium 860 may further contain other data or information, such as medical and health history of a wearer of the device 800, that may be useful in determining whether a medical condition is indicated. Further, the computer readable medium 860 may contain data corresponding to certain analyte baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the wearer of the device 800 based on data collected over a certain number of measurement periods. For example, the calculation and decision module 874 may generate a baseline concentration of a target blood analyte for each of a plurality of measurement periods by averaging the analyte concentration at each of the measurement periods measured over the course of a few days, and store those baseline concentrations in the computer readable medium 860 for later comparison. Baselines may also be generated by a remote server and transmitted to the wearable device 800 via communication interface 830. The calculation and decision module 874 may also, upon determining that a medical condition is indicated, generate one or more recommendations for the wearer of the device 800 based, at least in part, on consultation of a clinical protocol. Such recommendations may alternatively be generated by the remote server and transmitted to the device 800.

In some examples, the collected physiological parameter data, baseline profiles, health state information input by device wearers and generated recommendations and clinical protocols may additionally be input to a cloud network and be made available for download by a wearer's physician. Trend and other analyses may also be performed on the collected data, such as physiological parameter data and health state information, in the cloud computing network and be made available for download by physicians or clinicians.

Further, physiological parameter and health state data from individuals or populations of device wearers may be used by physicians or clinicians in monitoring efficacy of a drug or other treatment. For example, high-density, real-time data may be collected from a population of device wearers who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical condition is indicated, the alert module 876 may generate an alert via the user interface 820. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

IV. Illustrative Imaging Agents Including Functionalized Nanodiamond Particles

In some examples, the wearable devices described above obtain at least some of the health-related information by detecting properties of an imaging agent, for example, microparticles or nanoparticles that include doped nanodiamonds and that have been functionalized to selectively interact with an analyte. The doped nanodiamonds can include a variety of dopants, including dopants that act as "color centers." Color centers include dopants that can emit light in response to illumination of the dopants. Color centers can have specific optical properties that make them useful for imaging or use in imaging agents; for example, color centers in nanodiamonds can have narrow light emission spectra. Color center dopants can include a variety of carbon and non-carbon atoms, a variety of crystal defects, and combinations of atoms and defects. For example, a color center in a nanodiamond could include a negatively-charged, positively-charged, multiply-charged, or neutral silicon vacancy center. Herein, the phrase "silicon-vacancy nanodiamond" is used to refer to a nanodiamond that includes at least one silicon vacancy center.

The nanodiamonds can be functionalized by attaching a bioreceptor designed to selectively bind or otherwise recognize a particular analyte. For example, nanodiamonds may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. The bioreceptor (or a combination of bioreceptors) could be chosen to cause the nanodiamonds to selectively interact with an analyte that includes a target of the bioreceptor. For example, a bioreceptor that selectively interacts with a protein or other element that is expressed by cancer cells could be chosen to be attached to nanodiamonds to enable the use of the functionalized nanodiamonds to detect cancer cells. The functionalized nanodiamonds can be introduced into the person's blood stream by injection, ingestion, inhalation, transdermally, or in some other manner.

Nanodiamonds can be functionalized by attaching bioreceptors to the nanodiamonds using a variety of methods. Bioreceptors can be attached to the surface of the nanodiamonds by covalent bonds, adsorption, electrostatic attraction, Van der Waals forces, or by some other mechanism. The surface of the nanodiamonds could be treated or altered to facilitate binding of bioreceptors. In some examples, the surface of the nanodiamonds could be altered such that the diamond lattice is terminated in carboxyl groups. In some examples, the surface of the nanodiamonds could be treated with a strong oxidative acid. Additionally or alternatively, a coating or other substance could contain the nanodiamonds, be bound to the surface of the nanodiamonds, or otherwise attach to the nanodiamonds such that bioreceptors can be attached to the coating or other substance, such that the bioreceptor is indirectly attached to the nanodiamonds. More than one bioreceptor could be attached to the nanodiamonds. In some examples, complexes of the same or different bioreceptors could be attached directly or indirectly to the nanodiamonds such that the nanodiamonds more selectively interacted with a target analyte.

The analyte could be a clinically-relevant analyte. A clinically-relevant analyte could be any analyte that, when present in or absent from the blood, or present at a particular concentration or range of concentrations, may be indicative of a medical condition or indicative that a medical condition may be imminent. For example, the clinically-relevant analyte could be an enzyme, hormone, protein, cell, or other biological element. In one relevant example, certain protein biomarkers expressed by a cell are known to be predictive of the cell being a cancer cell. By providing nanodiamonds functionalized with a bioreceptor that will selectively bind to these target protein biomarkers.

Color centers in a nanodiamond could include silicon vacancy centers. Silicon vacancy centers in diamond (SiV centers) can be characterized by emission of light having a narrow band of wavelengths (less than 15 nanometers full width at half-maximum) centered at approximately 738 nanometers. This emission can occur in response to illumination having any wavelength in a wide range of wavelengths, for example, from about 500 nanometers to about 710 nanometers. In some examples, SiV centers can absorb light through two-photon absorption. For example, the SiV centers could absorb two photons having wavelengths between approximately 1050 nanometers and approximately 1200 nanometers and emit light in response to the absorption of the two photons. Color centers in nanodiamond could include negatively-charged silicon vacancy centers, positively-charged silicon vacancy centers, neutral silicon vacancy centers, or multiply-charged silicon vacancy centers. Silicon vacancy centers having different charge states can have different respective optical properties.

Figure 9:
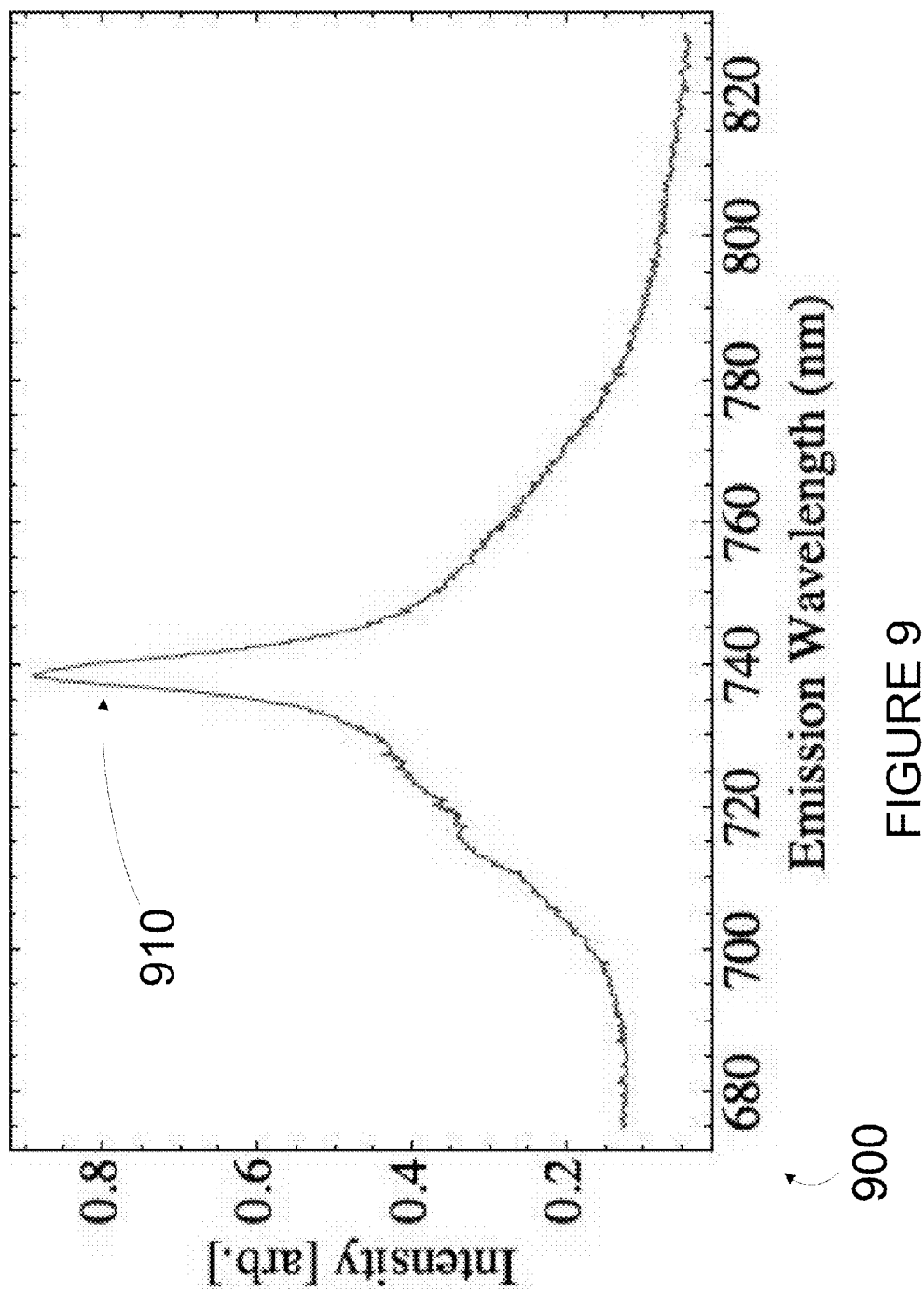
FIG. 9 is an emission spectrum of example silicon vacancy centers in diamond.

FIG. 9 shows an example emission spectrum 900 of silicon vacancy centers in diamond. The emission spectrum 900 was determined based on measurements of the light emitted by SiV centers in diamond in response to being illuminated by illumination having a wavelength of 532 nanometers. The emission spectrum 900 illustrates the zero-phonon emission line 910. The zero-phonon emission line 910 has a peak wavelength of about 738 nanometers and a full width at half-maximum of about 10 nanometers.

Individual SiV centers can preferentially absorb and/or emit light of certain polarizations relative to the orientation of the SiV center. For example, SiV centers can be more likely to absorb polarized light oriented parallel to an axis of the SiV center than polarized light having other orientations. This polarization-dependence of absorption can be related to wavelength; for example, the orientation of a preferred axis of absorption and/or the degree of preference in absorbing polarized light parallel to that axis of absorption could have one set of values for a first wavelength (e.g., 600 nanometers) and a second, different set of values for a second wavelength (e.g., 700 nanometers). Similarly, SiV centers can be more likely to emit light of a specific linear polarization relative to an axis of the SiV centers than light of other polarizations.

An imaging agent could include nanodiamonds that individually include single SiV centers. Additionally or alternatively, the imaging agent could include nanodiamonds that individually include a plurality of SiV centers that have a preferred orientation; that is, the orientations of SiV centers in individual nanodiamonds are not uniformly distributed, but are instead individually oriented such that there is a mean orientation of SiV centers in the nanodiamonds is detectably different from zero. It could be possible to detect and/or track the orientation of nanodiamonds containing a single SiV center and/or nanodiamonds containing SiV centers with a preferred orientation. For example, the direction and/or degree of polarization of light used to illuminate SiV center-containing nanodiamonds could be controlled to enable the detection of the orientation of the SiV center-containing nanodiamonds. Additionally or alternatively, the polarization of light emitted by SiV center-containing nanodiamonds could be detected to enable orientation detection.

An imaging agent could include a plurality of types of color-center-containing nanodiamonds functionalized to selectively interact with respective analytes in a biological environment. For example, an imaging agent could include a first set of SiV center-containing nanodiamonds functionalized to selectively interact with a first analyte and a second set of SiV center-containing nanodiamonds functionalized to selectively interact with a second analyte, where the SiV centers within an individual nanodiamond of the set of second nanodiamonds had a preferred orientation. The identity of an individual nanodiamond could be determined based on a difference in polarization specificity in the absorption and/or emission of light by SiV centers of the second set of nanodiamonds.

An imaging agent could additionally include nanodiamonds that contained color centers other than silicon vacancy centers. For example, an imaging agent could include nanodiamonds that contained nitrogen-vacancy centers. In some examples, differences in optical properties of color centers in different types of color-center-containing nanodiamonds could enable the detection of the identity of the type, among other properties, of detected color-center-containing nanodiamonds. For example, an imaging agent could include a first set of nanodiamonds that contained silicon vacancy centers (silicon-vacancy nanodiamonds) and a second set of nanodiamonds that contained nitrogen vacancy centers (nitrogen-vacancy nanodiamonds). A difference in optical properties between nitrogen vacancy centers and silicon vacancy centers (for example, a difference in emission spectra) could be detected to determine whether a detected nanodiamond is a silicon-vacancy nanodiamond or a nitrogen-vacancy nanodiamond.

In some examples, individual nanodiamonds could include more than one type of color center. For example, an individual nanodiamond could include at least one SiV center and at least one nitrogen vacancy center. In some examples, an imaging agent could include a plurality of sets of nanodiamonds, each set of nanodiamonds functionalized to selectively interact with a respective analyte in a biological environment. Each set of nanodiamonds could include nanodiamonds having a respective specified ratio of concentrations of color centers, e.g., a ratio of concentration of SiV centers to concentration of nitrogen vacancy centers. For example, an imaging agent could include a first set of nanodiamonds functionalized to selectively interact with a first analyte and including a first ratio of concentration of SiV centers to concentration of nitrogen vacancy centers. The imaging agent could include a second set of nanodiamonds functionalized to selectively interact with a second analyte and including a second ratio of concentration of SiV centers to concentration of nitrogen vacancy centers, where the second ratio is detectably different from the first ratio. The difference in ratios could be detected to identify whether a detected nanodiamond is from the first set or from the second set.

Imaging agent particles that include functionalized, doped nanodiamonds may additionally include other elements. Imaging agent particles could include biodegradable or non-biodegradable materials. For example, the particles may include polystyrene. Particles that include non-biodegradable materials may be provided with a removal means to prevent harmful buildup in the body. Generally, the particles may be designed to have a long half-life so that they remain in the vasculature or body fluids to enable their use in detecting analytes over an extended period of time. Depending on the lifetime of the particles, however, new batches of imaging agent particles may be periodically introduced into the biological environment.

Imaging agent particles can be used in diagnostic procedures, or even in therapy to destroy a specific target, such as antitumor therapy or targeted chemotherapy. The particles may be designed to remove from the body or destroy the target analyte once bound to the bioreceptor. Additional functional groups may be added to the particles to signal that the particles can be removed from the body through the kidneys, for example, once bound to the target analyte.

Further, the particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Those of skill in the art will understand the term "particle" in its broadest sense and that it may take the form of any fabricated material, a molecule, tryptophan, a virus, a phage, etc. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

Nanodiamonds may be produced by a variety of methods and may assume a variety of morphologies. In some examples, nanodiamonds are produced by detonation (detonation nanodiamonds, DNDs) of explosives. In these examples, dopants can be created in the DNDs by inclusions of dopant atoms and precursor chemicals within the mix of explosives used to create the nanodiamonds. In some examples, nanodiamonds are created through chemical vapor deposition (CVD) or physical vapor deposition (PVD) and dopants or other properties of the nanodiamonds are controlled by controlling properties of the CVD, PVD, or other processes used to create the nanodiamonds. Additionally or alternatively, dopants (including dopant atoms, dopant crystal defects, and other dopants) can be added to nanodiamonds after the creation of the nanodiamonds, for example, by exposing the nanodiamonds to an ion beam. Creation of a desired dopant or population of dopants in a nanodiamond can include other processes, for example, an annealing process following exposure to an ion beam or following some other process. Additional methods of fabricating doped, functionalized, color-center-containing nanodiamonds are anticipated.

An imaging agent that includes functionalized, dopant-containing nanodiamonds can include functionalized, dopant-containing polycrystalline nanodiamonds. That is, the nanodiamonds can comprise a plurality of crystal domains. Additionally or alternatively, the imaging agent could include monocrystalline functionalized, doped nanodiamonds. In some examples, nanodiamonds can have sizes between approximately 5 nanometers and 5 micrometers. For example, an imaging agent can include nanodiamonds having a mean size of approximately 35 nanometers.

The term "binding" is understood in its broadest sense to include any detectable interaction between an imaging agent particle and a target analyte. For example, some particles may be functionalized with compounds or molecules, such as fluorophores or autofluorescent, luminescent or chemiluminescent markers, which generate a responsive signal when the particles bind to the target analyte without the input of a stimulus. In other examples, the functionalized particles may produce a different responsive signal in their bound versus unbound state in response to an external stimulus, such as an electromagnetic, acoustic, optical, or mechanical energy. In some examples, binding of the particles could be detected by a change in the movement of the particles. For example, the orientation and/or location of the particles could be detectable, and the rotation and/or translation of the particles could be affected by binding of the particles. For example, unbound particles could exhibit changes in orientation at a certain rate, while bound particles could exhibit changes in orientation at a detectably lower rate, due to the inertia or other properties of the bound analyte.

Further, the particles may include a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect, orient, or otherwise selectively manipulate the particles in an area of a biological environment. Such collection may enhance the signal for detection and/or increase a signal-to-noise-ratio of detection by correlating modulation of the orientation, location, or other properties of the particles with a detected property of the particles (for example, the amplitude of an emitted light).

Figure 10:
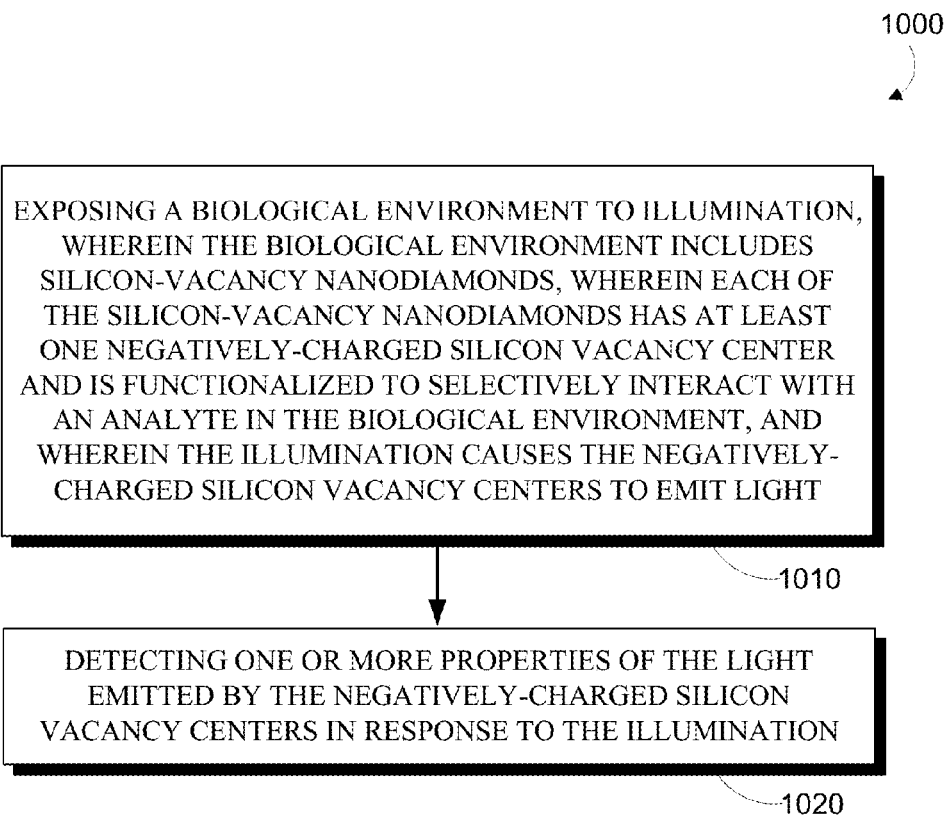
FIG. 10 is a flowchart of an example method.

V. Illustrative Methods for Detecting Silicon-Vacancy Nanodiamonds in a Biological Environment FIG. 10 is a flowchart of a method 1000 for operating a device to detect the presence, location, orientation, concentration, or other properties of silicon-vacancy nanodiamonds in a biological environment. Each silicon-vacancy nanodiamond in the biological environment includes at least one silicon vacancy center (at least one SiV center) and is functionalized to selectively interact with an analyte in the biological environment.

The method 1000 includes exposing the biological environment to illumination 1010 such that the SiV centers in the silicon-vacancy nanodiamonds are caused to emit light. This can include emitting illumination that includes light having wavelengths between approximately 500 nanometers and 710 nanometers, to excite the SiV centers through single-photon excitation. Additionally or alternatively, this can include emitting illumination that includes light having wavelengths between approximately 1050 nanometers and 1200 nanometers, to excite the SiV centers through two-photon excitation. Exposing the biological environment to illumination 1010 can include emitting illumination having a specified linear, circular, or other polarization. Further, exposing the biological environment to illumination 1010 can include emitting illumination having different properties at different points in time. For example, it could include emitting illumination having a first amplitude, wavelength, polarization, or other property at a first point in time and emitting illumination having a second amplitude, wavelength, polarization, or other property at a second point in time. Exposing the biological environment to illumination 1010 could additionally include emitting illumination such that some other element of the environment emitted light in response. For example, illumination could be emitted such that nitrogen vacancy centers in nanodiamonds in the biological environment emit light.

The method 1000 additionally includes detecting one or more properties of the light emitted by the SiV centers in response to the illumination 1020. This can include detecting the amplitude, wavelength, degree of polarization, orientation of polarization, location, or other properties of the illumination. It can also include detecting one or more properties of light emitted by the SiV centers at more than one point in time. For example, the location of light emitted by SiV centers in response to illumination could be detected at a plurality of points in time. The respective plurality of detected locations of emitted light could then be used to infer respective locations of SiV centers in the biological environment at the plurality of points in time.

The method 1000 could include additional steps or elements in addition to exposing the biological environment to illumination 1010 and detecting one or more properties of the light emitted by the SiV centers in response to the illumination 1020. For example, the method 1000 could include introducing the silicon-vacancy nanodiamonds into the biological environment (e.g., injecting, ingesting, transdermally transferring, or otherwise introducing the silicon-vacancy nanodiamonds into a lumen of vasculature of a human, applying the nanodiamonds to an in vitro or other non-human biological environment, or other methods). The method 1000 could include determining one or more properties of the silicon-vacancy nanodiamonds based on the detected one or more properties of the light emitted by the SiV centers. For example, the method 1000 could include determining the location of a silicon-vacancy nanodiamond based on the location of light emitted by the SiV centers. The method 1000 could further include determining one or more properties of the analyte based on determined one or more properties of the silicon-vacancy nanodiamond(s). For example, the determined location, orientation, or other properties of one or more silicon-vacancy nanodiamonds could be used to determine the location of one or more instances of the analyte. Other additional and/or alternative elements of method 1000 are anticipated.

The method 1000 could include illuminating fluorescent agents other than silicon-vacancy nanodiamonds and detecting light emitted by fluorescent agents other than silicon-vacancy nanodiamonds in response to illumination. For example, the method 1000 could include illuminating nitrogen vacancy centers in nitrogen-vacancy nanodiamonds and detecting at least one property of light emitted by the nitrogen vacancy centers in response to the illumination. In some examples, the silicon-vacancy nanodiamonds of method 1000 could include other color centers, like nitrogen vacancy centers, in addition to the SiV centers. Other additional fluorescent agents and/or steps related to the additional fluorescent agents are anticipated.

In some examples, the biological environment described in relation to the method 1000 above could be a portion of vasculature in a human body. For example, the biological environment could be a lumen of subsurface vasculature of a wearer of a device that is configured to implement and execute elements of the method 1000. In some examples, the analyte in the biological environment could be a cell. For example, the biological environment could be a tissue of a human, and the analyte could be a cancer cell. The silicon-vacancy nanodiamonds could be functionalized to selectively interact with the cancer cell by being attached to a bioreceptor that is selectively receptive to one or more elements of the cancer cell, e.g., a membrane-spanning protein. Other examples of biological environments, analytes, configurations of nanodiamond functionalization, and other elements are anticipated.

FIGS. 11A-11B, 12, 13, and 14 are partial cross-sectional side views of a human wrist illustrating the operation of various examples of a wrist-mounted device. In the example shown in FIGS. 11A and 11B, the wrist-mounted device 1100 includes a measurement platform 1110 mounted on a strap or wrist-band 1120 and oriented on the anterior side 1190 of the wearer's wrist. Measurement platform 1110 is positioned over a portion of the wrist where subsurface vasculature 1130 is easily observable. Functionalized, SiV center-containing functionalized nanodiamonds 1140 have been introduced into a lumen of the subsurface vasculature by one of the means discussed above. In this example, measurement platform 1110 includes a data collection system having both a light sensor 1150 and a light source 1160. FIG. 11A illustrates the state of the subsurface vasculature 1130 when wrist-mounted device 1100 is inactive. The state of the subsurface vasculature 1130 during detection is illustrated in FIG. 11B. At this time, light source 1160 is transmitting illumination 1162 into the portion of subsurface vasculature and light sensor 1150 is detecting one or more properties of an emitted light 1152 emitted by SiV centers in the functionalized nanodiamonds 1140 in response to the illumination 1162. The emitted light 1152 can have one or more properties related to one or more properties of the functionalized nanodiamonds 1140. One or more properties of the functionalized nanodiamonds 1140 can be related to one or more properties of an analyte in the sub surface vasculature 1130.

The wrist-mounted device 1100 could be configured to determine one or more properties of the functionalized nanodiamonds 1140 based on the detected one or more properties of the emitted light 1152. Additionally or alternatively, the wrist-mounted device 1100 could be configured to convey information about the detected one or more properties of the emitted light 1152 to another system, and the other system could be configured to determine one or more properties of the functionalized nanodiamonds 1140 based on the conveyed information. For example, the location of functionalized nanodiamonds 1140 in the subsurface vasculature 1130 could be determined based on the location of the emitted light 1152 (e.g., the light sensor 1150 could include a grid of light-sensing pixels, and the location of an individual functionalized nanodiamond 1140 could be determined by calculating a centroid of active pixels of the light sensor 1150 during a period when the light source 1160 is transmitting the illumination 1162).

The wrist-mounted device 1100 could be configured to determine one or more properties of the analyte in the subsurface vasculature 1130 based on determined one or more properties of the functionalized nanodiamonds 1140. Additionally or alternatively, the wrist-mounted device 1100 could be configured to convey information about the determined one or more properties of the functionalized nanodiamonds 1140 to another system, and the other system could be configured to determine one or more properties of the analyte based on the conveyed information. For example, the location of an individual instance of the analyte (e.g., a single cancer cell) in the subsurface vasculature 1130 could be determined based on the determined location(s) of one or more functionalized nanodiamonds 1140 over time. A correlation in the locations of more than one functionalized nanodiamonds 1140 over time could be used to determine that the more than one functionalized nanodiamonds 1140 are bound to the individual instance of the analyte and that the location of the individual instance of the analyte is proximate to the determined locations of the more than one functionalized nanodiamonds 1140.

Figure 12:
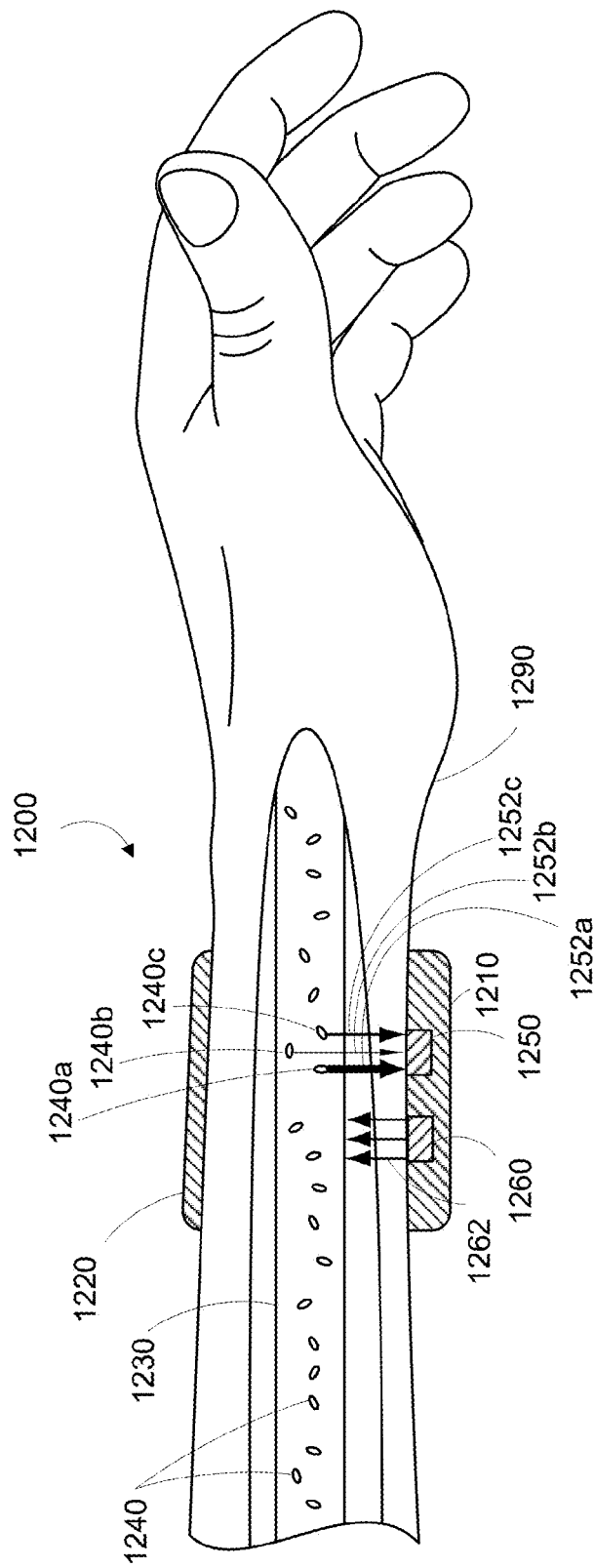
FIG. 12 is side partial cross-sectional view of a wrist-mounted device, while on a human wrist.

Similar to the system depicted in FIGS. 11A and 11B, FIG. 12 illustrates a wrist-mounted device 1200 including a measurement platform 1210 mounted on a strap or wrist-band 1220 and oriented on the anterior side 1290 of the wearer's wrist. In this example, measurement platform 1210 includes a data collection system having a light sensor 1250 and a light source 1260. Subsurface vasculature 1230 includes functionalized silicon-vacancy nanodiamonds 1240 that are configured to selectively interact with an analyte in the subsurface vasculature 1230. Each individual nanodiamond in the functionalized silicon-vacancy nanodiamonds 1240 includes at least one silicon vacancy center (SiV center), and the SiV center(s) in an individual silicon-vacancy nanodiamond has a preferred orientation (referred to herein as "orientable SiV nanodiamonds"). The state of the subsurface vasculature 1230 when measurement device 1200 is active during detection is illustrated in FIG. 12. At this time, light source 1260 is transmitting illumination 1262 into the portion of subsurface vasculature 1230 and light sensor 1250 is detecting one or more properties of emitted lights 1252*a*, 1252*b*, 1252*c* emitted by SiV centers in respective individual orientable SiV nanodiamonds 1240*a*, 1240*b*, 1240*c* of functionalized silicon-vacancy nanodiamonds 1240 in response to the illumination 1262. The emitted lights 1252*a*, 1252*b*, 1252*c* can have one or more properties related to one or more properties of respective individual orientable SiV nanodiamonds 1240*a*, 1240*b*, 1240*c*. One or more properties of the individual orientable SiV nanodiamonds 1240*a*, 1240*b*, 1240*c* can be related to one or more properties of respective analytes in the subsurface vasculature 1230.

The SiV center(s) in an individual silicon-vacancy nanodiamond having a preferred orientation (an orientable SiV nanodiamond) includes a configuration of one or more SiV centers in an individual nanodiamond such that light emitted by the SiV centers is at least partially polarized. An individual SiV center in diamond can emit polarized light having a specific orientation relative to the orientation of the individual SiV center in response to illumination. The amplitude and/or orientation of polarization of light emitted by an individual SiV center in diamond can also be related to the polarization and/or orientation of polarization of light illuminating the individual SV centers. Thus, an individual nanodiamond containing a single SiV center has a preferred orientation. Individual nanodiamonds containing more than one SiV center can have a preferred orientation depending on the orientation of the individual SiV centers within the individual nanodiamond. The preferred orientations of the example individual orientable SiV nanodiamonds 1240a, 1240b, 1240c in FIG. 12 are illustrated by the orientation of the ellipses used to illustrate the individual nanodiamonds in the subsurface vasculature 1300. So, individual orientable SiV nanodiamond 1240a has a vertical preferred orientation relative to the wrist-mounted device 1200, individual orientable SiV nanodiamond 1240b has a horizontal orientation relative to the wrist-mounted device 1200, and individual orientable SiV nanodiamond 1240c has an angled orientation relative to the wrist-mounted device 1200.

The use of functionalized orientable SiV nanodiamonds can allow for increased-contrast imaging relative to functionalized silicon-vacancy nanodiamonds containing SiV centers that do not have a preferred orientation. For example, it could be assumed that background tissues of the wearer (e.g., the walls of the subsurface vasculature) emit substantially unpolarized light in response to being illuminated by the light source 1260. The light sensor 1250 could be configured to detect the polarization of light emitted by the tissues of the wearer and by the functionalized nanodiamonds 1240, and detected light that is substantially polarized could be assumed to be associated with an individual orientable SiV nanodiamond of the functionalized nanodiamonds 1240. Additionally or alternatively, the light source 1260 could transmit illumination 1262 having different polarizations or other properties at respective points in time, and one or more properties of light emitted by the functionalized nanodiamonds 1240 could be detected by the light sensor 1152 at the respective points in time. The detected one or more properties of the emitted light could change between different points in the respective points in time, and one or more properties of the individual functionalized orientable SiV nanodiamonds could be determined based on the detected one or more properties of the emitted light at the respective points in time.

The wrist-mounted device 1200 could be operated to determine the orientation of individual functionalized orientable SiV nanodiamonds. In some examples, the light sensor 1250 could be configured to detect the polarization of light emitted by SiV centers in the functionalized nanodiamonds 1240 in response to illumination by the light source 1260. The detected polarization could be used to infer and/or determine the orientation of the individual functionalized orientable SiV nanodiamonds, e.g., 1240a, 1240b, 1240c. In some examples, the light source 1260 could transmit illumination 1262 having different specified polarizations or other properties at respective points in time, and one or more properties of light emitted by the functionalized nanodiamonds 1240 could be detected by the light sensor 1152 at the respective points in time. The detected one or more properties of the emitted light could change between different points in the respective points in time, and the orientation of the individual functionalized orientable SiV nanodiamonds could be determined based on the detected one or more properties of the emitted light and the specified polarization or other properties of the transmitted illumination 1262 at the respective points in time.

The binding of one or more individual functionalized orientable SiV nanodiamonds to an analyte could be determined based on a specified polarization of illumination emitted by the light source 1260 and/or one or more properties of light emitted by the SiV centers in the individual functionalized orientable SiV nanodiamonds. In some examples, the aforementioned information could be used to determine the orientation and/or relative orientation of individual functionalized orientable SiV nanodiamonds. The orientation over time of an individual functionalized orientable SiV nanodiamond over time could be used to infer that the nanodiamond is bound due to a detectable difference between the behavior (in terms of the change of orientation and/or relative orientation over time) of an unbound nanodiamond and a nanodiamond bound to the analyte. For example, an individual nanodiamond and an individual nanodiamond bound to the analyte could be assumed to change orientation according to a statistical model having one or more parameters that are different for the unbound nanodiamond and the bound nanodiamond/analyte complex (for example, a hydrodynamic volume, a relaxation time, an electrostatic radius, or some other parameter or variable). Other methods of determining whether an individual functionalized orientable SiV nanodiamond is bound to an analyte, using wrist-mountable device similar to the wrist-mountable device 1200 or using some other apparatus, are anticipated.

Figure 13:
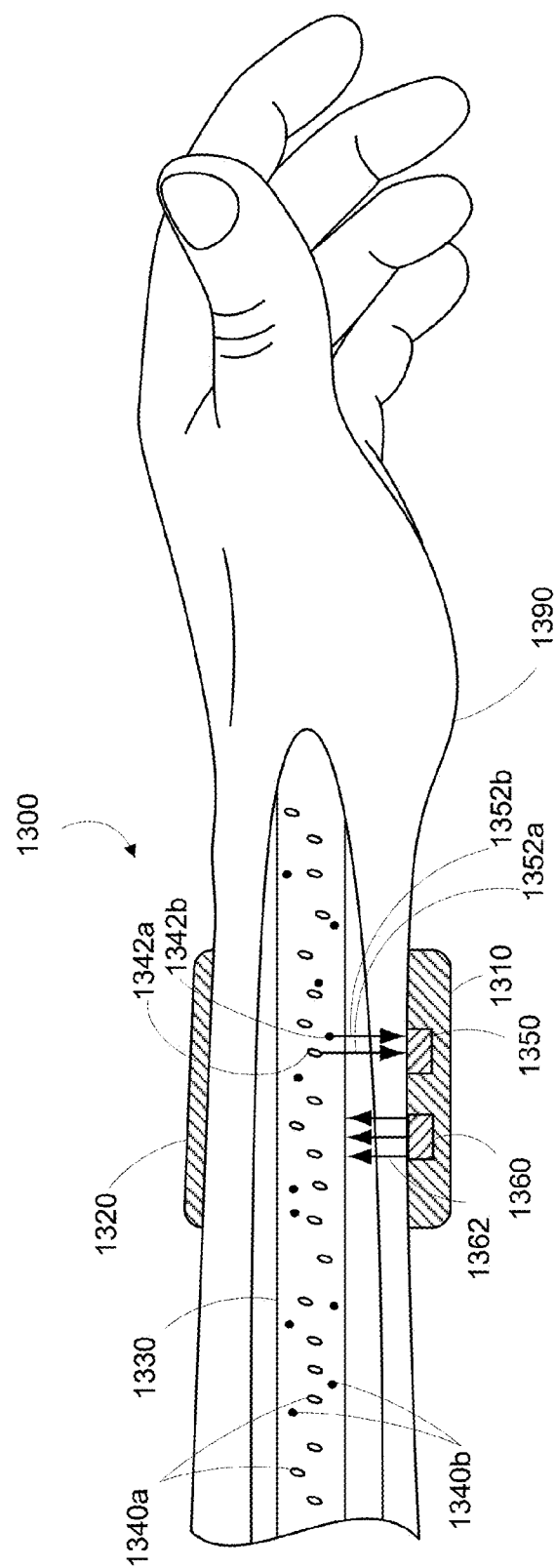
FIG. 13 is side partial cross-sectional view of a wrist-mounted device, while on a human wrist.

FIG. 13 illustrates an example in which the nanodiamonds in the subsurface vasculature 1330 include first functionalized nanodiamonds 1340a and second functionalized nanodiamonds 1340b configured to selectively interact with first and second analytes, respectively. The first functionalized nanodiamonds 1340a are silicon-vacancy nanodiamonds that each contain at least one silicon vacancy center (SiV center) and the second functionalized nanodiamonds 1340b are nitrogen-vacancy nanodiamonds that each contain at least one nitrogen vacancy center. FIG. 13 additionally illustrates a wrist-mounted device 1300 including a measurement platform 1310 mounted on a strap or wristband 1320 and oriented on the anterior side 1390 of the wearer's wrist. In this example, measurement platform 1310 includes a data collection system having a light sensor 1350 and a light source 1360.

The state of the subsurface vasculature 1330 when measurement device 1300 is active during detection is illustrated in FIG. 13. At this time, light source 1360 is transmitting illumination 1362 into the portion of subsurface vasculature 1330 and light sensor 1350 is detecting one or more properties of emitted lights 1352a, 1352b emitted by color centers of respective individual functionalized nanodiamonds 1342a, 1342b of the respective first and second functionalized nanodiamonds 1340a, 1340b in response to the illumination 1362. The emitted lights 1352a, 1352b can have one or more properties related to one or more properties of respective functionalized nanodiamonds 1340a, 1340b. One or more properties of the functionalized nanodiamonds 1340a, 1340b can be related to one or more properties of respective analytes in the subsurface vasculature 1330.

The transmitted illumination 1362 could be such that nitrogen vacancy centers in diamond (in addition to SiV centers) emit light. Additionally or alternatively, the light source 1360 could be configured to produce additional illumination that can cause nitrogen vacancy centers in diamond to emit light. The light sensor 1350 could be configured to detect one or more properties of light emitted by nitrogen vacancy centers in diamond. Other examples of the wrist-mounted device 1300 interacting with other fluorophores and/or color centers using the light source 1350 and light sensor 1360 are anticipated. Other fluorophores and/or color centers include but are not limited to fluorescent proteins, Raman dyes, point defects in diamond, line defects in diamond, vacancies in diamond, non-carbon atoms in diamonds, combinations of vacancies and non-carbon atoms in diamond, defects and/or dopant atoms in crystals other than diamond, and engineered conductive and/or non-conductive nanostructures.

It could be determined whether an individual nanodiamond in the subsurface vasculature 1330 is a silicon-vacancy nanodiamond 1340a or a nitrogen-vacancy nanodiamond 1340b based on one or more properties of light emitted by the individual nanodiamond and detected using the light sensor 1350. In some examples, an emission spectrum of light emitted by an individual nanodiamond could be detected and the detected emission spectrum could be used to determine whether the individual nanodiamond is a silicon-vacancy nanodiamond 1340a or a nitrogen-vacancy nanodiamond 1340b (e.g., by determining that a characteristic emission peak in the detected emission spectrum corresponded to an emission peak of SiV centers in diamond rather than an emission peak of nitrogen vacancy centers in diamond).

Other properties of the detected emitted light, including but not limited to polarization, amplitude, wavelength, amplitude(s) at a specified wavelength(s), polarization(s) at a specified wavelength(s), or other properties could be used to determine that the individual nanodiamond is a silicon-vacancy nanodiamond 1340a or a nitrogen-vacancy nanodiamond 1340b. Additionally or alternatively, one or more properties of the illumination 1362 transmitted by the light source 1360 could be controlled to enable the determination that individual nanodiamonds in the subsurface vasculature are silicon-vacancy nanodiamonds 1340a or nitrogen-vacancy nano diamonds 1340b.

The determination that one or more individual nanodiamonds is a silicon-vacancy nanodiamond 1340a or a nitrogen-vacancy nanodiamond 1340b could be used to determine one or more properties of one or more analytes in the subsurface vasculature 1330. For example, the location of an analyte in the subsurface vasculature 1330 could be determined based on correlated determined locations of proximate individual nanodiamonds in the subsurface vasculature; the identity of the analyte as being an instance of the first analyte or the second analyte could be determined based on the determination that the proximate individual nanodiamonds are silicon-vacancy nanodiamonds 1340a or a nitrogen-vacancy nanodiamonds 1340b, respectively.

FIG. 14 illustrates an example in which the nanodiamonds in the subsurface vasculature 1430 include first, second, and third functionalized nanodiamonds 1440a, 1440b, 1440c that contain color centers and that are configured to selectively interact with first and second analytes, respectively. At least one of the first, second, and third functionalized nanodiamonds 1440a, 1440b, 1440c includes SiV centers. Each of the first, second, and third functionalized nanodiamonds 1440a, 1440b, 1440c have specified respective concentrations of silicon vacancy centers (SiV centers) and of nitrogen vacancy centers, such that each of the first, second, and third functionalized nanodiamonds 1440a, 1440b, 1440c have a respective unique ratio of concentration of SiV centers to concentration of nitrogen vacancy centers. FIG. 14 additionally illustrates a wrist-mounted device 1400 including a measurement platform 1410 mounted on a strap or wristband 1420 and oriented on the anterior side 1490 of the wearer's wrist. In this example, measurement platform 1410 includes a data collection system having a light sensor 1450 and a light source 1460.

The state of the subsurface vasculature 1430 when measurement device 1400 is active during detection is illustrated in FIG. 14. At this time, light source 1460 is transmitting illumination 1462 into the portion of subsurface vasculature 1430 and light sensor 1450 is detecting one or more properties of emitted lights 1452a, 1452b, 1452c emitted by color centers of respective individual functionalized nanodiamonds 1442a, 1442b, 1442c of the respective first, second, and third functionalized nanodiamonds 1440a, 1440b, 1440c in response to the illumination 1462. The emitted lights 1452a, 1452b, 1452c can have one or more properties related to one or more properties of respective functionalized nanodiamonds 1440a, 1440b, 1440c. One or more properties of the functionalized nanodiamonds 1440a, 1440b, 1440c can be related to one or more properties of respective analytes in the subsurface vasculature 1430.

The transmitted illumination 1462 could be such that nitrogen vacancy centers in diamond (in addition to SiV centers) emit light. Additionally or alternatively, the light source 1460 could be configured to produce additional illumination that can cause nitrogen vacancy centers in diamond to emit light. The light sensor 1450 could be configured to detect one or more properties of light emitted by nitrogen vacancy centers in diamond. Other examples of the wrist-mounted device 1400 interacting with other fluorophores and/or color centers using the light source 1450 and light sensor 1460 are anticipated. Other fluorophores and/or color centers include but are not limited to fluorescent proteins, Raman dyes, point defects in diamond, line defects in diamond, vacancies in diamond, non-carbon atoms in diamonds, combinations of vacancies and non-carbon atoms in diamond, defects and/or dopant atoms in crystals other than diamond, and engineered conductive and/or non-conductive nanostructures.

It could be determined that an individual nanodiamond in the subsurface vasculature 1430 s one of the first, second, or third nanodiamonds 1440a, 1440b, 1440c based on one or more properties of light emitted by the individual nanodiamond and detected using the light sensor 1450. In some examples, an emission spectrum of light emitted by an individual nanodiamond could be detected and the detected emission spectrum could be used to determine the ratio of concentration of SiV centers to concentration of nitrogen vacancy centers in the individual nanodiamond (e.g., by performing a calculation based on the amplitude of the emitted light at two different wavelengths, e.g., at a peak emission wavelength of SiV centers in diamond and at a peak emission wavelength of nitrogen vacancy centers in diamond). The determined ratio of concentration of SiV centers to concentration of nitrogen vacancy centers in the individual nanodiamond could then be used to determine that the individual nanodiamond is one of the first, second, or third nanodiamonds 1440a, 1440b, 1440c.

Other properties of the detected emitted light, including but not limited to polarization, amplitude, wavelength, amplitude(s) at a specified wavelength(s), polarization(s) at a specified wavelength(s), or other properties could be used to determine that the individual nanodiamond is one of the first, second, or third nanodiamonds 1440a, 1440b, 1440c. Additionally or alternatively, one or more properties of the illumination 1462 transmitted by the light source 1460 could be controlled to enable the determination that individual nanodiamonds in the subsurface vasculature are from the set of first, second, or third nanodiamonds 1440a, 1440b, 1440c.

The determination that one or more individual nanodiamonds is one of the first, second, or third nanodiamonds 1440a, 1440b, 1440c could be used to determine one or more properties of one or more analytes in the subsurface vasculature 1430. For example, the location of an analyte in the subsurface vasculature 1430 could be determined based on correlated determined locations of proximate individual nanodiamonds in the subsurface vasculature; the identity of the analyte as being an instance of the first, second, or third analyte could be determined based on the determination that the proximate individual nanodiamonds re one of the first, second, or third nanodiamonds 1440a, 1440b, 1440c, respectively. Additionally or alternatively, one or more of the first, second, and third analytes could be components of an analyte of interest, e.g., the analyte of interest could be a cancer cell and the first, second, and third analytes could be unique markers on the surface of the cancer cell. One or more properties of the analyte of interest could be determined based on determined information about the first, second, and third analytes.

Note that sets of functionalized nanodiamonds present in the subsurface vasculature 1430 can include more or fewer than the three functionalized nanodiamond types 1440a, 1440b, 1440c illustrated in the examples of FIG. 14. Subsets of the nanodiamonds in the subsurface vasculature 1430 could selectively interact with different or similar analytes or subsections of analytes. Subsets of the functionalized nanodiamonds could selectively interact with other functionalized nanodiamonds, subsections of functionalized nanodiamonds, or other imaging agents present in the subsurface vasculature 1430. Other configurations and/or uses of functionalized nanodiamonds in a biological environment (e.g., subsurface vasculature) are anticipated.

Note that functionalized nanodiamonds may include at least one SiV center having a preferred orientation and additional, non-SiV color centers. For example, functionalized nanodiamonds may include at least one SiV center and at least one nitrogen vacancy center, and the at least one SiV center could have a preferred orientation. Further, the other color centers could, themselves, have a preferred orientation, and the preferred orientation of the other color centers could be parallel to the preferred orientation of the SiV centers or could have some other relationship with the preferred orientation of the SiV color centers. An imaging agent could include a plurality of type of functionalized nanodiamonds, where each type of functionalized nanodiamonds had similar concentrations of SiV centers and other color center, but where a relationship between a preferred orientation of SiV centers and a preferred orientation of other color centers in each type of functionalized nanodiamonds is unique and capable of being detected to identify which set of functionalized nanodiamonds an individual nanodiamond belonged to. Other configurations and uses of functionalized nanodiamonds are anticipated.

FIGS. 11, 12, 13, and 14 illustrate paths of the transmitted illumination (1162, 1262, 1362, 1462) transmitted by the light source (1160, 1260, 1360, 1460) and the emitted lights (1152, 1252a, 1252b, 1252c, 1352a, 1352b, 1452a, 1452b, 1452c) detected by the light sensor (1150, 1250, 1350, 1450) that do not overlap. However, in some instances, the light source (1160, 1260, 1360, 1460) and the light detector (1150, 1250, 1350, 1450) may be angled towards each other so that they are illuminating and sensing from essentially the same area of subsurface vasculature. Other configurations of light sources, light sensors, light paths, and other elements are anticipated. Further, it is anticipated that more than one light source or light sensor may be included to enable the embodiments and methods disclosed herein.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A method comprising:
exposing a biological environment to illumination from a light source in a wearable device, wherein the illumination comprises excitation light having a wavelength between 1050 and 1200 nanometers, wherein silicon-vacancy nanodiamonds have been introduced into the biological environment, wherein each of the silicon-vacancy nanodiamonds has at least one silicon vacancy center and is functionalized to selectively interact with an analyte in the biological environment, and wherein the excitation light is absorbed by the silicon vacancy centers through two-photon absorption and causes the silicon vacancy centers to emit light in a band of wavelengths centered at approximately 738 nanometers and having a full width at half-maximum of less than 15 nanometers; and detecting, by a light sensor in the wearable device, one or more properties of the light emitted by the silicon vacancy centers in response to the excitation light.

2. The method of claim 1, wherein the biological environment is a portion of subsurface vasculature.

3. The method of claim 1, wherein the analyte is a cell.

4. The method of claim 1, further comprising introducing the silicon-vacancy nanodiamonds into the biological environment.

5. The method of claim 1, further comprising:
determining one or more properties of the silicon-vacancy nanodiamonds in the biological environment based on the detected one or more properties of the light emitted by the silicon vacancy centers; and
determining a property of the analyte based on the determined one or more properties of the silicon-vacancy nanodiamonds.

6. The method of claim 1, wherein the silicon vacancy centers have a preferred orientation, wherein detecting one or more properties of the light emitted by the silicon vacancy centers comprises detecting a polarization of the emitted light, further comprising:
detecting binding of a silicon-vacancy nanodiamond to the analyte based on at least the detected one or more properties of the emitted light.

7. The method of claim 1, wherein the silicon vacancy centers have a preferred orientation, wherein the illumination has a specified polarization, further comprising:
detecting binding of a silicon-vacancy nanodiamond to the analyte based on at least the specified polarization and the detected one or more properties of the emitted light.

8. The method of claim 1, wherein nitrogen-vacancy nanodiamonds have been introduced into the biological environment, and wherein each of the nitrogen-vacancy nanodiamonds has at least one nitrogen vacancy center and is functionalized to selectively interact with a second analyte in the biological environment, further comprising:
exposing the biological environment to additional illumination, and wherein the additional illumination causes the nitrogen vacancy centers to emit light;
detecting one or more properties of the light emitted by the nitrogen vacancy centers in response to the additional illumination; and
determining whether a nanodiamond in the biological environment was a silicon-vacancy nanodiamond or a nitrogen-vacancy nanodiamond based on at least the detected one or more properties of the light emitted by the silicon vacancy centers and the detected one or more properties of the light emitted by the nitrogen vacancy centers.

9. The method of claim 8, wherein each of the silicon-vacancy nanodiamonds has at least one nitrogen vacancy center, wherein the ratio of the concentration of silicon vacancy centers to the concentration of nitrogen vacancy centers in the silicon-vacancy nanodiamonds is a first ratio, wherein each of the nitrogen-vacancy nanodiamonds has at least one silicon vacancy center, wherein the ratio of the concentration of silicon vacancy centers to the concentration of nitrogen vacancy centers in the nitrogen-vacancy nanodiamonds is a second ratio, wherein the first and second ratios are different.

10. A wearable device comprising:
a light source that can direct excitation light having a wavelength between 1050 and 1200 nanometers to a biological environment into which silicon-vacancy nanodiamonds have been introduced, wherein each silicon-vacancy nanodiamond has at least one silicon vacancy center and is functionalized to selectively interact with an analyte in the biological environment, and wherein the excitation light is absorbed by the silicon vacancy centers through two-photon absorption and causes the silicon vacancy centers to emit light in a band of wavelengths centered at approximately 738 nanometers and having a full width at half-maximum of less than 15 nanometers; and
a light sensor that can detect one or more properties of the light emitted by the silicon vacancy centers in response to the excitation light.

11. The wearable device of claim 10, wherein the biological environment is a portion of subsurface vasculature.

12. The wearable device of claim 11, wherein the device further comprises:
a housing, wherein the light source and light sensor are disposed in the housing; and
a mount, wherein the mount is configured to mount the housing to an external surface proximate the portion of subsurface vasculature such that the light source can illuminate the silicon-vacancy nanodiamonds in the portion of subsurface vasculature and the light sensor can detect the one or more properties of the light emitted by the silicon vacancy centers.

13. The wearable device of claim 10, further comprising a controller, wherein the controller is configured to:
operate the light source to illuminate the biological environment,
operate the light sensor to detect the one or more properties of light emitted by the silicon vacancy centers,
determine one or more properties of the silicon-vacancy nanodiamonds in the biological environment based on the detected one or more properties of the emitted light; and
determine a property of the analyte based on the determined one or more properties of the silicon-vacancy nanodiamonds.

14. The wearable device of claim 10, wherein the silicon vacancy centers have a preferred orientation, wherein detecting one or more properties of the light emitted by the silicon vacancy centers comprises detecting a polarization of the emitted light, and further comprising a controller configured to:
operate the light source to illuminate the biological environment,
operate the light sensor to detect one or more properties of the light emitted by the silicon vacancy centers,
detect binding of a silicon-vacancy nanodiamond to the analyte based on at least the detected one or more properties of the emitted light.

15. The wearable device of claim 10, wherein each of the silicon-vacancy nanodiamonds has at least one nitrogen vacancy center, wherein each of the silicon-vacancy nanodiamonds has a ratio of the concentration of silicon vacancy centers to the concentration of nitrogen vacancy centers, wherein the light source is configured to expose the biological environment to additional illumination, wherein the additional illumination causes the nitrogen vacancy centers to emit light, wherein the light sensor is configured to detect one or more properties of the light emitted by the nitrogen vacancy centers in response to the additional illumination, and wherein the ratio of the concentration of silicon vacancy centers to the concentration of nitrogen vacancy centers can be determined based on the detected one or more properties of the light emitted by the nitrogen vacancy centers and the detected one or more properties of the light emitted by the silicon vacancy centers.

* * * * *